(12) United States Patent
Kim et al.

(10) Patent No.: US 10,322,136 B2
(45) Date of Patent: Jun. 18, 2019

(54) COMPOSITION FOR INHIBITING GROWTH OR PROLIFERATION OF CHRONIC MYELOGENOUS LEUKEMIA CANCER STEM CELLS, AND SCREENING METHOD THEREFOR

(71) Applicant: HIROSHIMA UNIVERSITY, Hiroshima (JP)

(72) Inventors: Seong Jin Kim, Seoul (KR); Kazuhito Naka, Hiroshima (JP)

(73) Assignee: HIROSHIMA UNIVERSITY, Hiroshima (JP)

( * ) Notice: Subject to any disclaimer, the term of this patent is extended or adjusted under 35 U.S.C. 154(b) by 0 days.

(21) Appl. No.: 15/560,885

(22) PCT Filed: Mar. 25, 2016

(86) PCT No.: PCT/KR2016/003029
§ 371 (c)(1),
(2) Date: Sep. 22, 2017

(87) PCT Pub. No.: WO2016/159575
PCT Pub. Date: Oct. 6, 2016

(65) Prior Publication Data
US 2018/0117057 A1  May 3, 2018

(30) Foreign Application Priority Data
Mar. 27, 2015 (KR) .................. 10-2015-0043305

(51) Int. Cl.
| | |
|---|---|
| *A61K 31/545* | (2006.01) |
| *A61K 31/506* | (2006.01) |
| *G01N 33/50* | (2006.01) |
| *A61K 45/06* | (2006.01) |
| *A61K 31/43* | (2006.01) |
| *A61P 35/02* | (2006.01) |
| *C12Q 1/6886* | (2018.01) |

(52) U.S. Cl.
CPC ............ *A61K 31/545* (2013.01); *A61K 31/43* (2013.01); *A61K 31/506* (2013.01); *A61K 45/06* (2013.01); *A61P 35/02* (2018.01); *C12Q 1/6886* (2013.01); *G01N 33/50* (2013.01); *G01N 33/5011* (2013.01); *C12Q 2600/136* (2013.01); *C12Q 2600/158* (2013.01); *G01N 2333/4703* (2013.01); *G01N 2333/705* (2013.01); *G01N 2440/14* (2013.01)

(58) Field of Classification Search
CPC .................................................. A61K 31/545
USPC ........................................................ 514/209
See application file for complete search history.

(56) References Cited

U.S. PATENT DOCUMENTS

2015/0005361 A1    1/2015  Slukvin et al.

OTHER PUBLICATIONS

Naka, Nature, 2010, vol. 463, pp. 676-680.*
Naka, Nature, 2010, 463, 676-680.*
Luckner, European Journal of Pharmaceutics and Biopharmaceutics, 2005, vol. 59, No. 1, pp. 17-24.*
Catriona, Physiology (Bethesda, Md.) (2010), 25(6), 364-77.*
Meredith, Journal of Membrane Biology (2007), 213(2), 79-88.*
Venkatesh et al., J. Pharm. Sci. 89, 145-54 (2000).*
Freshney (Culture of Animal Cells, A Manual of Basic Technique, Alan R. Liss, Inc., 1983, New York, p. 4).*
Naka, Nature communications (2015), 6, 8039.*
Hawkins, Pediatr Res 57: 430-437, 2005.*
EP Search Report, EP Patent Application No. 16773356.7, dated Mar. 9, 2018.
Naka, Kazuhito et al., "TGF-β-FOXO signalling maintains . . .", Nature, 2010, vol. 463, pp. 676-680.
Calabretta, Bruno et al., "Inhibition of autophagy: a new strategy to enhance . . .", Leukemia & lymphoma, 2011, vol. 52, No. S1, pp. 54-59.
Nakanishi, Takeo et al., "Carrier-mediated Transport of Oligopeptides . . .", Cancer Research, 1997, vol. 57, No. 18, pp. 4118-4122.
Luckner, Petra et al., "Interaction of 31 β-lactam antibiotics with . . .", European Journal of Pharmaceutics and Biopharmaceutics, 2005, vol. 59, No. 1, pp. 17-24.
Naka, Kazuhito et al., "Dipeptide species regulate p38MAPK . . .", Nature Communications, [Published online], Aug. 20, 2015, vol. 6, Article No. 8039, inner pp. 1-14.
International Search Report for PCT/KR2016/003029, dated Sep. 9, 2016.
English Translation of Form PCT/ISA/237 for PCT/KR2016/003029, dated Sep. 9, 2016.

* cited by examiner

*Primary Examiner* — Nizal S Chandrakumar
(74) *Attorney, Agent, or Firm* — Casimir Jones, SC; Robert A. Goetz

(57) ABSTRACT

Provided are a composition for inhibiting growth or proliferation of chronic myelogenous leukemia (CML) cancer stem cells, a pharmaceutical composition for preventing or treating CML, a method for preventing or treating CML, and a method of screening for a growth or proliferation inhibitor of CML cancer stem cells by blocking nutrient signaling in CML cancer stem cells.

6 Claims, 29 Drawing Sheets

FIG. 2

CML/Normal Ratios

|  | KLS+ Immature | KLS- Progenitor | Lin+ Differentiated |
|---|---|---|---|
| Ala-Leu | 38.19* | 3.57* | 1.30 |
| Ala-Phe | 25.65* | 2.26 | 1.41 |
| Ala-Tyr | 3.15 | 1.45 | 1.00 |
| Ala-Val | 26.80 | 5.00 | 1.68 |
| Arg-Ala | 2.44 | 1.85 | 0.33 |
| Asp-Leu | 5.23* | 10.29* | 2.16 |
| Gln-Leu | 17.92* | 4.34 | 2.99 |
| Gly-Leu | 14.42 | 5.60 | 3.72* |
| Gly-Phe | 6.32* | 8.94* | 2.21 |
| Ile-Ala | 10.62* | 16.58 | 2.52* |
| Ile-Gln | 7.23* | 2.27 | 1.35 |
| Ile-Tyr | 1.61 | 5.99 | 2.72 |
| Ile-Val | 10.73* | 19.28 | 1.61 |
| Leu-Ala | 50.34* | 5.69 | 1.26 |
| Leu-Glu | 6.20* | 1.98 | 1.54 |
| Leu-Phe | 1.23 | 2.92* | 0.79 |
| Leu-Ser | 18.14* | 3.34 | 1.84 |
| Leu-Tyr | 1.88 | 0.99 | 0.89 |
| Phe-Ala | 7.14* | 6.36 | 1.92 |
| Phe-Val | 13.81* | 6.23 | 1.57* |
| Ser-Leu | 10.58 | 4.32 | 3.91 |
| Ser-Phe | 11.05* | 7.11* | 1.31 |
| Ser-Tyr | 6.87* | 2.82* | 2.16 |
| Thr-Phe | 1.50 | 6.71* | 2.81 |
| Thr-Val | 32.43* | 10.98 | 1.84* |
| Val-Leu | 21.58* | 3.18 | 1.46 |
| Val-Phe | 3.33* | 2.12 | 0.99 |
| Val-Val | 2.54* | 4.69* | 1.08 | p-S6 p-S208 p-Smad3 (Ser208)-
Foxo3a p-Smad3 (Ser208)-
Foxo3a

COMPOSITION FOR INHIBITING GROWTH OR PROLIFERATION OF CHRONIC MYELOGENOUS LEUKEMIA CANCER STEM CELLS, AND SCREENING METHOD THEREFOR

TECHNICAL FIELD

The present disclosure relates to a composition for inhibiting growth or proliferation of chronic myelogenous leukemia cancer stem cells, a pharmaceutical composition for preventing or treating chronic myelogenous leukemia, a method of preventing or treating chronic myelogenous leukemia, and a method of screening for a growth or proliferation inhibitor of chronic myelogenous leukemia cancer stem cells.

BACKGROUND ART

Treatment strategies for chronic myelogenous leukemia which accounts for about 15~20% of adult leukemias are largely divided into anticancer chemotherapy and hematopoietic stem cell transplantation. The anticancer chemotherapy involves regulating the excessive number of leukocytes and symptoms such as splenomegaly by using interferon alpha and hydroxyurea, and low-dose cytarabine. However, since Gleevec, the first target therapy, was introduced into the treatment of chronic myelogenous leukemia, Gleevec has become the standard treatment of chronic myelogenous leukemia. However, Gleevec was found to have problems that it is expensive, use of a high dose thereof causes serious side-effects, and resistance according to use of Gleevec occurs to cause decreased sensitivity to Gleevec. Furthermore, the biggest problem of Gleevec is that it cannot inhibit formation of cancer stem cells which is a cause of recurrence, and therefore, Gleevec cannot be a therapeutic agent for complete cure. Of hematopoietic stem cell transplantation, allogeneic hematopoietic stem cell transplantation is the only method for complete treatment of chronic myelogenous leukemia, but a survival rate after transplantation of hematopoietic stem cells is influenced by a patient' age, a disease state at the time of transplantation, transplantation from unrelated donor, difference in the sex of donor and recipient, and the period from diagnosis to transplantation. The biggest problem is that rates of transplant-related mortality and morbidity reach 10~70%. Therefore, it is urgent to develop a more effective therapeutic agent for chronic myelogenous leukemia.

Meanwhile, CML cancer stem cells are an origin of CML cancer cells and also a cause of CML disease. When formation of CML cancer stem cells is inhibited, recurrence of chronic myelogenous leukemia may be prevented and a survival rate of an individual with this disease may be increased. To inhibit formation of CML cancer stem cells, a nutrient acquisition pathway which is not required in normal HSCs but critical to maintenance of CML cancer stem cells may be a target for removing CML stem cells and treating chronic myelogenous leukemia. However, a relationship between treatment of chronic myelogenous leukemia and nutrient signaling of CML cancer stem cells has not been yet disclosed.

DETAILED DESCRIPTION OF THE INVENTION

Technical Problem

An aspect provides a composition for inhibiting growth or proliferation of chronic myelogenous leukemia cancer stem cells.

Another aspect provides a composition for preventing or treating chronic myelogenous leukemia.

Still another aspect provides a method of preventing or treating chronic myelogenous leukemia of a subject, and a method of inhibiting chronic myelogenous leukemia cancer stem cells.

Still another aspect provides a method of screening for a growth or proliferation inhibitor of chronic myelogenous leukemia cancer stem cells.

Technical Solution

An aspect provides a composition for inhibiting growth or proliferation of chronic myelogenous leukemia (CML) stem cells, the composition including a substance blocking nutrient signaling of CML stem cells as an active ingredient.

The term "chronic myelogenous leukemia (CML)" refers to a hematologic stem cell disease caused by uncontrolled growth of bone marrow cells in the bone marrow and excessive accumulation of leukocytes, and includes a disease caused by abnormal proliferation of hematopoietic stem cells with Philadelphia chromosome in the bone marrow.

The term "chronic myelogenous leukemia cancer stem cell (CML stem cell)" refers to a cell that may initiate chronic myelogenous leukemia, and is an origin of mature CML cells. The 'CML cancer stem cell' may be also called 'CML stem cell' or 'leukemia-initiating cell (LIC)'.

The term "active ingredient" refers to an ingredient that is included in an amount enough to block nutrient signaling of CML cancer stem cells, excluding impurities.

The term "nutrient signaling" refers to all intracellular responses related to regulation of maintenance or change of nutrients such as ATP, amino acids, oxygen, etc., which are closely related with the balance of cell synthesis and degradation metabolisms for cell proliferation or survival.

The term "substance blocking nutrient signaling of CML cancer stem cells" refers to a substance capable of reducing, modifying, inactivating, or inhibiting reactions in CML cancer stem cells, which are related to regulation of nutrients essential for maintenance or proliferation of CML cancer stem cells.

The substance blocking nutrient signaling of CML cancer stem cells may be a dipeptide transporter inhibitor.

The term "dipeptide transporter" refers to a protein or polypeptide having an activity of transporting a dipeptide which is a molecule composed of two amino acids into a cell. The dipeptide transporter may be a dipeptide transporter of Slc15a family, for example, a protein encoded by one or more genes selected from the group consisting of Slc15a1, Slc15a2, Slc15a3, and Slc15a4. Further, the dipeptide transporter may be specifically a protein encoded by Slc15a2 gene.

The term "dipeptide transporter inhibitor" refers to a substance capable of inhibiting a function that the dipeptide transporter transports dipeptides into CML cancer stem cells. The dipeptide transporter inhibitor may reduce or interrupt internalization of dipeptides into CML cancer stem cells. The dipeptide transporter inhibitor may be any compound, protein, amino acid, peptide, virus, carbohydrate, lipid, nucleic acid, etc. without limitation, as long as it is a substance capable of reducing or interrupting internalization of dipeptides into CML cancer stem cells. These inhibitors may hinder binding of dipeptides and dipeptide transporters or inhibit phosphorylation of a particular metabolic pathway by dipeptides.

The substance blocking nutrient signaling of CML cancer stem cells may be a substrate specific to the dipeptide transporter. The inhibitor may be specific to the dipeptide transporter, and compete with the dipeptide for binding to the transporter. As a result, the inhibitor inhibits binding of the dipeptide transporter and dipeptide, thereby inhibiting intracellular uptake of dipeptides. Further, the substance blocking nutrient signaling of CML cancer stem cells may be, for example, a substrate specific to Slc15a2 protein, and inhibit dipeptide transport function of Slc15a2 protein.

The substance blocking nutrient signaling of CML cancer stem cells may inhibit activation of Smad3 pathway induced by dipeptides. CML cancer stem cells internalize dipeptides via the dipeptide transporters, and internalized dipeptides may activate Smad3 pathway in CML cancer stem cells. Thus, the substance blocking nutrient signaling of CML cancer stem cells may inactivate Smad3 pathway in CML cancer stem cells, for example, phosphorylation of Smad3 at position Ser208. The substance blocking nutrient signaling of CML cancer stem cells may specifically inhibit phosphorylation of Ser208 of Smad3.

The substance blocking nutrient signaling of CML cancer stem cells may be beta-lactam (β-lactam) antibiotics. The β-lactam antibiotics may collectively refer to substances having beta-lactamase (β-lactamase)-inhibiting activity, and the substances include a β-lactam structure in their molecules. The substance blocking nutrient signaling of CML cancer stem cells may be penicillin antibiotics or cephalosporin antibiotics, for example, one or more selected from the group consisting of cefadroxil, cefaclor, cyclacillin, cephradine, cephalexin, moxalactam, ceftibuten, dicloxacillin, amoxycillin, metampicillin, cloxacillin, ampicillin, cefixime, cefamandole, oxacillin, cefmetazole, 7-aminocephalosporanic acid, cefaloridine, and cefuroxime axetil. Further, the substance blocking nutrient signaling of CML cancer stem cells may be specifically cefadroxil. The β-lactam antibiotics may be replaced by pharmaceutically acceptable salts thereof.

The substance blocking nutrient signaling of CML cancer stem cells may be a dipeptide analogue. The dipeptide analogue may be a substance that has a similar structure to the dipeptide and serves as a substrate of the dipeptide transporter, particularly, Slc15A transporter, but is not metabolized by cells. Further, the dipeptide analogue may be, for example, glycylsarcosine or a pharmaceutically acceptable salt thereof.

The composition for inhibiting growth or proliferation of CML cancer stem cells may further include a tyrosine kinase inhibitor (TKI). That is, the active ingredient of the pharmaceutical composition may be a combination of the substance blocking nutrient signaling of CML cancer stem cells, for example, the dipeptide transporter inhibitor and the tyrosine kinase inhibitor.

The tyrosine kinase inhibitor refers to a substance inhibiting tyrosine kinase. The tyrosine kinase inhibitor may be a BCR-ABL tyrosine kinase inhibitor. The BCR-ABL tyrosine kinase may be a BCR-ABL fusion protein having tyrosine kinase activity, which is produced by BCR-ABL gene produced by chromosomal translocation.

The tyrosine kinase inhibitor may be 4-[(4-methyl-1-piperazinyl)methyl]-N-[4-methyl-3-[[4-(3-pyridinyl)-2-pyrimidinyl]amino]phenyl]-benzamide, N-(2-chloro-6-methylphenyl)-2-[[6-[4-(2-hydroxyethyl)-1-piperazinyl]-2-methyl-4-pyrimidinyl]amino]-5-thiazole carboxamide monohydrate, 4-methyl-N-[3-(4-methyl-1H-imidazol-1-yl)-5-(trifluoromethyl)phenyl]-3-[(4-pyridin-3-yl pyrimidin-2-yl)amino]benzamide, 4-[(2,4-dichloro-5-methoxyphenyl)amino]-6-methoxy-7-[3-(4-methylpiperazin-1-yl)propoxy]quinoline-3-carbonitrile, or a pharmaceutically acceptable salt thereof. Further, the tyrosine kinase inhibitor may be, for example, one or more selected from the group consisting of imatinib, nilotinib, dasatinib, bosutinib, and pharmaceutically acceptable salts thereof, and specifically, imatinib or a pharmaceutically acceptable salt thereof. The pharmaceutically acceptable salt of imatinib may be, for example, an imatinib mesylate salt.

Another aspect provides a pharmaceutical composition for preventing or treating CML, the composition including the substance blocking nutrient signaling of CML cancer stem cells as an active ingredient.

The substance blocking nutrient signaling of CML cancer stem cells is the same as described above.

With regard to the pharmaceutical composition, the substance blocking nutrient signaling of CML cancer stem cells may be the dipeptide transporter inhibitor. The dipeptide transporter inhibitor is the same as described above. The dipeptide transporter inhibitor may decrease a dipeptide level in the CML cancer stem cells, compared with that in CML cancer stem cells treated with no inhibitor.

The dipeptide transporter inhibitor may be β-lactam antibiotics, and one or more selected from the group consisting of cefadroxil, cefaclor, cyclacillin, cephradine, cephalexin, moxalactam, ceftibuten, dicloxacillin, amoxycillin, metampicillin, cloxacillin, ampicillin, cefixime, cefamandole, oxacillin, cefmetazole, 7-aminocephalosporanic acid, cefaloridine, and cefuroxime axetil.

With regard to the pharmaceutical composition, CML may be caused by, for example, CML cancer stem cells. Further, CML may be recurred by resistance of a subject to Bcr-Abl tyrosine kinase.

The composition for inhibiting growth or proliferation of CML cancer stem cells may further include a tyrosine kinase inhibitor (TKI). That is, the active ingredient of the pharmaceutical composition may be a combination of the substance blocking nutrient signaling of CML cancer stem cells and the tyrosine kinase inhibitor.

The tyrosine kinase inhibitor may be a BCR-ABL tyrosine kinase inhibitor. The BCR-ABL tyrosine kinase may be a BCR-ABL fusion protein having tyrosine kinase activity, which is produced by BCR-ABL gene produced by chromosomal translocation.

The tyrosine kinase inhibitor may be 4-[(4-methyl-1-piperazinyl)methyl]-N-[4-methyl-3-[[4-(3-pyridinyl)-2-pyrimidinyl]amino]phenyl]-benzamide, N-(2-chloro-6-methylphenyl)-2-[[6-[4-(2-hydroxyethyl)-1-piperazinyl]-2-methyl-4-pyrimidinyl]amino]-5-thiazole carboxamide monohydrate, 4-methyl-N-[3-(4-methyl-1H-imidazol-1-yl)-5-(trifluoromethyl)phenyl]-3-[(4-pyridin-3-yl pyrimidin-2-yl)amino]benzamide, 4-[(2,4-dichloro-5-methoxyphenyl)amino]-6-methoxy-7-[3-(4-methylpiperazin-1-yl)propoxy]quinoline-3-carbonitrile, and pharmaceutically acceptable salts thereof. Further, the tyrosine kinase inhibitor may be, for example, one or more selected from the group consisting of imatinib, nilotinib, dasatinib, bosutinib, and pharmaceutically acceptable salts thereof, and specifically, imatinib and a pharmaceutically acceptable salt thereof. The pharmaceutically acceptable salt of imatinib may be an imatinib mesylate salt.

The pharmaceutical composition may have any pharmaceutical form. The pharmaceutical composition may be, for example, in a form suitable for oral administration such as a tablet, a capsule, a pill, a powder, a sustained release formulation, a solution, or a suspension, for parenteral administration such as a sterile solution, a suspension, or an emulsion, for topical administration such as an ointment or a cream, or for rectal administration such as a suppository.

The composition may be a tablet, a pill, an injectable formulation, or a combination thereof. The composition may be in a unit dosage form suitable for single administration of precise dosages.

The pharmaceutical composition includes a general pharmaceutically acceptable carrier or excipient and the compound described herein as an active ingredient. The appropriate carrier may include an inert diluent or filler, water and various organic solvents. The pharmaceutical composition may include additional components, for example, a flavor, a binder, an excipient, etc. in addition to the active ingredient.

A range of an administration dose of the pharmaceutical composition may vary depending on a patient's weight, age, sex, health conditions, diet, administration time, administration method, excretion rate, and severity of disease, etc.

Still another aspect provides a method of preventing or treating CML of a subject, or a method of inhibiting growth or proliferation of CML cancer stem cells in the subject, including administering to the subject a pharmaceutically effective amount of the substance blocking nutrient signaling of CML cancer stem cells.

With regard to the method, the 'chronic myelogenous leukemia (CML) cancer stem cells', 'CML', or 'substance blocking nutrient signaling' is the same as described above.

The method may include administering to the subject the substance blocking nutrient signaling of CML cancer stem cells or the dipeptide transporter inhibitor. The dipeptide transporter inhibitor is the same as described above. Further, the dipeptide transporter inhibitor may inhibit, for example, uptake of the dipeptide into CML cancer stem cells or phosphorylation of Smad3 at position Ser208.

The term "subject", as used herein, refers to a subject in need of treatment or prevention of the disease or in need of inhibition of growth or proliferation of CML cancer stem cells. Specifically, the subject may be a human or a non-human primate, a mammal such as mice, rats, dogs, cats, horses, cattle, etc., and more specifically, a human.

The subject may be a subject having CML or CML cancer stem cells, or a subject having a possibility of having the same.

The "pharmaceutically effective amount" may be determined according to factors including a kind and severity of a disease to be treated, a patient's age and sex, drug sensitivity, administration time, administration route, and excretion rate, treatment period, co-administered drug, and other factors well known in the medical field, and easily determined by those skilled in the art as an amount that exhibit the maximum effect without causing side effects, considering all the factors described above.

The "administration" is not limited, as long as it is an administration method that allows the composition to reach a target tissue or cell. The administration may be performed by any method known in the art, for example, via an oral or parenteral route. A daily dose may be, but is not limited to, about 0.0001 mg/kg to about 100 mg/kg, and preferably, about 0.001 mg/kg to 10 mg/kg, and administered once or several times a day, and appropriately controlled by those skilled in the art.

Further, the method may include administering to a subject a pharmaceutically effective amount of a combination of the tyrosine kinase inhibitor and the substance blocking nutrient signaling of CML cancer stem cells, instead of the substance blocking nutrient signaling of CML cancer stem cells. The tyrosine kinase inhibitor and the substance blocking nutrient signaling of CML cancer stem cells are the same as described, respectively. The substance blocking nutrient signaling of CML cancer stem cells may be specifically the dipeptide transporter inhibitor. The dipeptide transporter inhibitor is the same as described above.

With regard to the method, the tyrosine kinase inhibitor and the substance blocking nutrient signaling of CML cancer stem cells, for example, the dipeptide transporter inhibitor may be co-administered. The co-administration means that the substance blocking nutrient signaling of the CML cancer stem cells is administered in a sufficiently short time so as to enhance effectiveness of the tyrosine kinase inhibitor. For example, the tyrosine kinase inhibitor is first administered, and the substance blocking nutrient signaling of the CML cancer stem cells, for example, the dipeptide transporter inhibitor may be secondly administered, or vice versa. Further, the tyrosine kinase inhibitor and the substance blocking nutrient signaling of the CML cancer stem cells, for example, the dipeptide transporter inhibitor may be administered at the same time.

Still another aspect provides a method of screening for a growth or proliferation inhibitor of CML cancer stem cells, the method including contacting a growth or proliferation inhibitor candidate of CML cancer stem cells with CML cancer stem cells, and measuring an expression level of Slc15A2 mRNA or protein, or a level of the dipeptide in the CML cancer stem cells.

The term "screening" refers to finding of a substance having a particular property such as sensitivity or activity with respect to a particular chemical material such as antibiotics, enzymes, low molecular weight chemical materials, etc.

The term "growth or proliferation inhibitor candidate of CML cancer stem cells" may be an individual nucleic acid, protein, extract or natural product, or compound that is predicted to inhibit growth or to prevent proliferation of CML cancer stem cells or randomly selected according to an usual selection method.

A method of measuring the expression level of Slc15A2 mRNA may be, for example, reverse transcriptase polymerase chain reaction, competitive reverse transcriptase polymerase chain reaction, real-time reverse transcriptase polymerase chain reaction, RNase protection assay, Northern blotting, or DNA chip, but is not limited thereto. The method of measuring the expression level of the protein may be, for example, Western blotting, ELISA, radioimmunoassay, radial immunodiffusion, Ouchterlony immunodiffusion, rocket immunoelectrophoresis, immunohistostaining, immunoprecipitation assay, complement fixation assay, FACS, or protein chips, but is not limited thereto.

A method of measuring the level of the dipeptide in CML cancer stem cells may be a method known in the art, for example, RT-PCR Western blotting, ELISA, radioimmunoassay, radial immunodiffusion, Ouchterlony immunodiffusion, rocket immunoelectrophoresis, immunohistostaining, immunoprecipitation assay, complement fixation assay, FACS, or protein chips.

The CML cancer stem cells may be short term (ST)-CML cancer stem cells or long term (LT)-CML cancer stem cells, and specifically, LT-CML cancer stem cells.

The method of screening for the growth or proliferation inhibitor of CML cancer stem cells may further include determining the inhibitor candidate as the growth or proliferation inhibitor of CML cancer stem cells when the expression level of Slc15A2 mRNA or protein is significantly decreased in a group treated with the inhibitor candidate, as compared with a control group which is not treated with the inhibitor candidate. The term "control group which is not treated with the inhibitor candidate" refers to CML cancer stem cells which are not treated with the growth or proliferation inhibitor candidate of CML cancer stem cells, and CML cancer stem cells having a parallel relationship with the candidate-treated group. That is, the control group may be CML cancer stem cells which are not treated with any material or which are treated with a negative material other than the growth or proliferation inhibitor of CML cancer stem cells.

Further, the method of screening for the growth or proliferation inhibitor of CML cancer stem cells may further include determining the inhibitor candidate as the growth or proliferation inhibitor of CML cancer stem cells when a group treated with the inhibitor candidate shows a similar or low expression level of Slc15A2 mRNA or protein, as compared with a positive control group which is treated with a substance known as the growth or proliferation inhibitor of CML cancer stem cells. The positive control group which is treated with the substance known as the growth or proliferation inhibitor of CML cancer stem cells refers to CML cancer stem cells which are treated with a compound known to show an inhibitory effect on growth or proliferation of CML cancer stem cells.

The method of screening for the growth or proliferation inhibitor of CML cancer stem cells is based on the fact that in CML cancer stem cells, phosphorylation of Smad3 at position Ser208 supports maintenance of CMS stem cells by mRNA of Slc15A2 which is a dipeptide transporter, but phosphorylation of Smad3 at position Ser208 does not influence in normal HSCs.

The method of screening for the growth or proliferation inhibitor of CML cancer stem cells is possible in both in vitro and in vivo. In vivo, contacting the growth or proliferation inhibitor candidate of CML cancer stem cells with CML cancer stem cells may be replaced by administering the candidate to a subject having CML cancer stem cells. The subject may be CML animals, for example, mammals excluding humans, specifically, mice.

Still another aspect provides a method of screening for a growth or proliferation inhibitor of CML cancer stem cells, the method including contacting a growth or proliferation inhibitor candidate of CML cancer stem cells with CML cancer stem cells, and measuring a phosphorylation level of S208 of Smad3 in the CML cancer stem cells.

A method of measuring the phosphorylation level is not limited, but, for example, electrophoresis, Fluorescence analysis, mass spectrometry, immunoassay, PCR, or Western blotting may be used.

The CML cancer stem cells may be ST (short term)-CML cancer stem cells or LT (long term)-CML cancer stem cells, and specifically, LT-CML cancer stem cells.

The method of screening for the growth or proliferation inhibitor of CML cancer stem cells may further include determining the inhibitor candidate as the growth or proliferation inhibitor of CML cancer stem cells when the phosphorylation level of S208 of Smad3 is significantly decreased in a group treated with the inhibitor candidate, as compared with a control group which is not treated with the inhibitor candidate. The term "control group which is not treated with the inhibitor candidate" refers to CML cancer stem cells which are not treated with the growth or proliferation inhibitor candidate of CML cancer stem cells, and CML cancer stem cells having a parallel relationship with the candidate-treated group. That is, the control group may be CML cancer stem cells which are not treated with any material or which are treated with a negative material other than the growth or proliferation inhibitor of CML cancer stem cells.

Further, the method of screening for the growth or proliferation inhibitor of CML cancer stem cells may further include determining the inhibitor candidate as the growth or proliferation inhibitor of CML cancer stem cells when a group treated with the inhibitor candidate shows a similar phosphorylation level of S208 of Smad3, as compared with a positive control group which is treated with a substance known as the growth or proliferation inhibitor of CML cancer stem cells. The positive control group which is treated with the substance known as the growth or proliferation inhibitor of CML cancer stem cells refers to CML cancer stem cells which are treated with a compound known to show an inhibitory effect on growth or proliferation of CML cancer stem cells.

The method of screening for the growth or proliferation inhibitor of CML cancer stem cells is based on the fact that in CML cancer stem cells in vitro or in vivo, phosphorylation of Smad3 at position Ser208 supports maintenance of CMS stem cells, but phosphorylation of Smad3 at position Ser208 does not influence in normal HSCs. According to the screening method of the present disclosure, a novel therapeutic agent for CML may be readily developed in an inexpensive and simple manner.

Advantageous Effects of the Invention

According to a composition for inhibiting growth or proliferation of CML cancer stem cells according to an aspect, growth or proliferation of CML cancer stem cells may be effectively inhibited by blocking nutrient signaling of CML cancer stem cells.

According to a pharmaceutical composition for preventing or treating CML according to another aspect, the composition may be efficiently used in the treatment of CML by blocking nutrient signaling of CML cancer stem cells in a subject.

According to a method of preventing or treating CML according to still another aspect, CML in a subject may be efficiently prevented or treated.

According to a method of screening for a therapeutic agent for CML according to still another aspect, the method may be effectively used in the exploration and development of the therapeutic agent for CML.

DESCRIPTION OF THE DRAWINGS

FIGS. 1 and 2 show metabolomic analysis results of KLS$^+$, KLS$^-$ and Lin$^+$ cells from CML-affected (Tal1-tTAxTRE-BCR-ABL1) mice (n=4; in each of three independent experiments) and normal healthy (Tal1-tTA) littermates (n=6; in each of two independent experiments) at 5 weeks post DOX withdrawal, in which CML cancer stem cells accumulated specific dipeptides which are not found in normal HSCs or differentiated CML cells:

FIG. 1 represents scaled intensity values for (A) metabolites related to glycolysis, (B) amino acids, and (C) dipeptides [+, mean value; box, quartile limits; horizontal line across box, median value; error bars, maximum and minimum of distribution; dot, extreme data point].

FIG. 2 represents ratios of the indicated dipeptide levels in CML vs normal hematopoietic stem cells of the indicated subsets. Red-shaded values indicate an increase in expression in CML cells of >10-fold; light red, >5-fold; light blue, <0.5-fold *P<0.05.

FIG. 3 shows Duolink® in situ PLA (D-PLA) imaging of Raptor-Ser863 and S6 phosphorylation in LT-CML cancer stem cells treated with vehicle (Cont), GlySar (5 μM), or cefadroxil (Cefa; 5 μM) for 30 minutes. Rapa (rapamycin; 100 nM) is a technical positive control for suppression of mTORC1 signaling pathway and S6 phosphorylation thereby. Nuclei were visualized by using DAPI. Scale bar, 10 μm.

FIG. 4 shows quantification result of the dot number of p-S6 per single LT-CML cancer stem cell which was measured from the experiment of FIG. 3 using Duolink® image tool software. Red line: dot/experimented (n)/average number of total cells of a group. *, P<0.00005 (compared with control).

FIG. 5 shows results of metabolomic analyses of dipeptide species in KLS$^+$ cells isolated from normal healthy littermates (n=6 mice in each of two independent experiments) and CML-affected mice (n=4 mice in each of three independent experiments) that received either vehicle (Cont) or cefadroxil (Cefa).

FIG. 6 shows quantification results of in vitro colony-forming capacity of LT-CML cancer stem cells and normal HSCs which were co-cultured on OP-9 stromal cells under hypoxic (3% $O_2$) conditions and treated with either vehicle (Cont) or cefadroxil (Cefa; 5 μM) for 5 days. Data are the mean colony number±s.d. (n=3) and are representative of three experiments.

FIG. 7 shows next-generation RNA sequencing analysis results of mRNA expression of Slc15a2 dipeptide transporter gene, and (A) RPKM ratio for mouse chr.16 vs Slc15a2 of cell subsets indicated, and (B) mapped transcriptome data.

FIG. 8 shows (A) Duolink® in situ PLA (D-PLA) imaging of (top) Smad2/3 C-terminal phosphorylation and (bottom) interaction between Foxo3a and Smad2 or Smad3 in LT-CML stem cells [Ab(–): technical negative control using a single mouse anti-Smad3 antibody; Nuclei were visualized using DAPI; Scale bar, 10 μm], and (B) quantification result of dot number/single LT-CML cancer stem cell in the bottom panel of (A) from the three experiments.

FIG. 9 shows (A) D-PLA imaging and (B) quantification result of Smad3 phosphorylation at the indicated sites in freshly isolated LT-CML cancer stem cells.

FIG. 10 shows (A) D-PLA imaging and (B) quantification result of Smad3 Ser423/425 and Smad3 Ser208 phosphorylation in the indicated CML cell subsets.

FIG. 11 shows flow cytometric quantification result of the indicated GFP$^+$KLS$^+$ CML cell subpopulations (red rectangles) among total GFP$^+$CML cells (top), and GFP$^+$LT$^-$ CML stem cells (red rectangles) among GFP$^+$CML$^-$KLS$^+$ cells (bottom), isolated from recipient mice.

FIG. 12 shows quantification of the frequency of GFP$^+$ LT$^-$CML stem cells among the GFP$^+$CML$^-$KLS$^+$ cells, as measured in FIG. 8(B). Data are the mean percentage of GFP$^+$LT$^-$CML cancer stem cells±s.d. (n=3).

FIG. 13 shows (A) D-PLA imaging and (B) quantification result of Smad3 Ser423/425 and Smad3 Ser208 phosphorylation in LT-CML stem cells treated for 30 min with DMSO (control) or Ly364947 (LY; 5 μM) [Scale bar, 10 μm. *, P<0.00005 (compared with control)].

FIG. 14 shows (A) D-PLA imaging and (B) quantification result of Smad3 Ser208 phosphorylation in LT-CML cancer stem cells treated for 30 min with vehicle (Cont), GlySar (5 μM), or cefadroxil (Cefa; 5 μM). Rapa (rapamycin; 100 nM) was used for inhibiting mTORC1 pathway [*, P<0.00005 compared with control; NS, not significant; Scare bar, 10 μm].

FIG. 15 shows (A) D-PLA imaging and (B) quantification result of Smad3 Ser208 and Smad3 Ser423/425 phosphorylation in LT-CML cancer stem cells and LT-normal HSCs.

FIG. 16 shows quantification results of in vitro colony-forming capacity of LT-CML cancer stem cells which were cultured in vitro for 5 days with either vehicle (Cont) or cefadroxil (Cefa; 5 μM) in the presence or absence of IM (1 μM). Data are the mean colony number±s.d. (n=3) and are representative of three experiments.

FIG. 17 shows a survival curve of CML-affected mice receiving IM and/or cefadroxil. At 8 days post transplantation, CML-affected mice received (1) vehicle alone; (2) vehicle+cefadroxil (36 mg/kg/day); (3) vehicle+IM (100 mg/kg/day); or (4) IM+cefadroxil. Results shown are cumulative data obtained from three independent experiments.

FIG. 18 is a diagram outlining the proposed role of dipeptide signal transduction in LT-CML cancer stem cell maintenance. Dipeptide species internalized by Slc15a2 dipeptide transporter may initiate nutrient signaling activating Smad3 pathway.

FIG. 25 shows mean number±s.d. (n=3) of GFP/BCR-ABL1+CML-KLS$^+$ cells among total GFP/BCR-ABL1+CML cells (n=3). FIG. 26 shows a survival rate of new recipient mice that received serial transplantation of GFP/BCR-ABL1+CML-KLS$^+$ cells (3×10$^4$ cells per recipient) derived from the CML-affected mice of FIG. 25 that had been treated with vehicle or Cefa.

FIG. 27 shows result of in vitro treatment of vehicle (−) or 5 µM Cefa (+) for 5 days, and FIG. 28 shows result of in vitro treatment of vehicle (−) or 5 µM Cefa (+) for 3 days (24 hours after Cefa treatment, vehicle, 1 µM IM, or 500 nM dasatinib (Dasa) was added, respectively).

MODE OF THE INVENTION

Figure 1A:
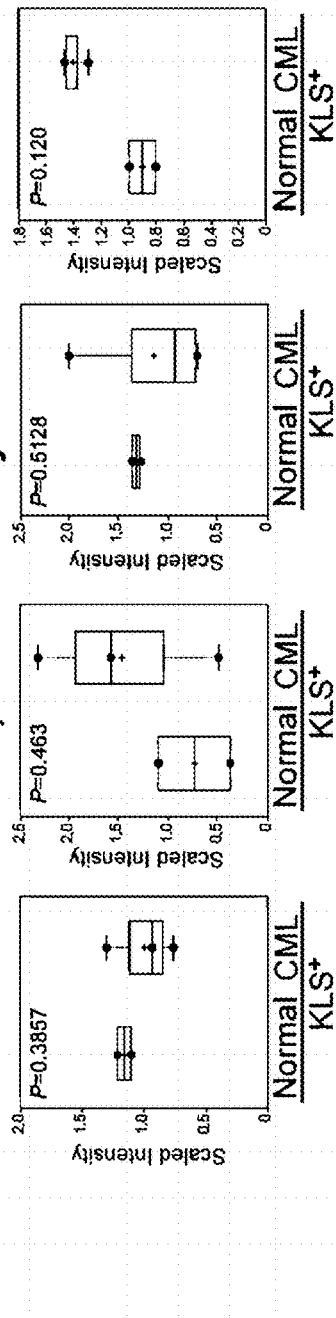

Hereinafter, the present invention will be described in more detail. However, these Examples are for illustrative purposes only, and the scope of the present invention is not intended to be limited by these Examples.

Experimental Methods

The following experimental methods were used in Examples, unless otherwise mentioned.

1. Preparation of CML Mouse Models

Several different mouse models of CML-like disease were employed in the study.

First, a tetracycline (tet)-inducible CML mouse model was used to induce CML disease. Tal1-tTA mice (JAX database strain, #006209) and TRE-BCR-ABL1 transgenic mice (JAX database strain, #006202), both of the FVB/N genetic background, were purchased from the Jackson Laboratory. Tal1-tTA and TRE-BCR-ABL1 transgenic mice were interbred to generate Tal1-tTA×TRE-BCR-ABL1 double-transgenic mice. These double-transgenic mice were maintained in cages supplied with drinking water containing 20 mg/L of doxycycline (Sigma-Aldrich). At 5 weeks after birth, expression of the BCR-ABL1 oncogene was induced by replacing the doxycycline-containing drinking water with normal drinking water. CML-like disease developed in the double-transgenic mutants about 5 weeks after doxycycline withdrawal. These animals were designated as "tetracycline-inducible CML-affected mice".

To establish our Foxo3a-deficient tet-inducible CML mouse model, Foxo3a-deficient mice 42 (C57BL/6; F5) were crossed with Tal-tTA and TRE-BCR-ABL1 transgenic mice that were backcrossed for five generations in the C57BL/6 background, respectively.

BCR-ABL1 transduction/transplantation-based CML model (BCR-ABL1 CML mice) was also used. Briefly, normal KLS$^+$ cells (4-5×10$^3$ cells per recipient mouse) were transduced with the human BCR-ABL1-ires GFP retrovirus and transplanted into irradiated (9 Gy) recipient C57BL/6 mice (Sankyo-Lab Service, Tsukuba, Japan). CML-like disease developed in these recipients at 12-20 days post transplantation.

To examine in vivo effects of the combined administration of IM+cefadroxil, BCR-ABL1-CML-affected mice received vehicle alone [artificial gastric fluid solution (900 ml ddH$_2$O containing 2.0 g of NaCl, 7 ml of conc. HCl, and 3.2 g of pepsin)], or imatinib mesylate (IM; Gleevec® 100 mg/kg/day; Novartis) in vehicle and/or cefadroxil (36 mg/kg/day; Sigma-Aldrich) in vehicle. Treatment was delivered by oral gavage on days 8 to 90 post transplantation. To examine the effect of single administration of Ly2228820, BCR-ABL1-CML-affected mice received vehicle, or Ly2228820 (2.5 mg kg$^{-1}$ every three days; Axon Medchem) in vehicle, by oral gavage on days 8 to 60 days post transplantation. To examine the effect of combined administration of dasatinib+Ly2228820, tet-inducible CML-affected mice received vehicle alone, or dasatinib (5 mgKg$^{-1}$day$^{-1}$; Brystol-Myers Squibb) in vehicle on days 1 to 30 post DOX withdrawal, and/or Ly2228820 (2.5 mg kg$^{-1}$ every three days; Axon Medchem) in vehicle on days 7 to 28 post DOX withdrawal by oral gavage. All animal care was in accordance with the guidelines for animal and recombinant DNA experiments of Kanazawa University.

2. Cell Sorting

Bone marrow (BM) mononuclear cells (MNCs) were isolated from the two hindlimbs of tet-inducible CML-affected mice (Tal1-tTA+ TRE-BCR-ABL1+) and normal healthy littermate mice (Tal1-tTA+) at 5 weeks after DOX withdrawal. BM MNCs were first incubated with anti-FcγIII/II receptor (2.4G2) antibody (BD Biosciences), and then with anti-Sca-1 (E13-161.7)-PE, anti-CD4 (L3T4)-FITC, anti-CD8 (53-6.7)-FITC, anti-B220 (RA3-6B2)-FITC, anti-TER119 (Ly-76)-FITC, anti-Gr-1 (RB6-8C5)-FITC, and anti-Mac1 (M1/70)-FITC (all purchased from BD Biosciences); anti-CD48 (HM48-1)-APC-Cy7 and anti-CD150/SLAM (TC15-12F12.2)-Pacific blue (both purchased from BioLegend); and anti-cKit (ACK2)-APC and anti-CD135/Flk2/Flt3 (A2F10)-biotin (both purchased from eBiosciences) antibodies. Biotinylated primary antibodies were visualized using Streptavidin-PE-Cy7 (BD Biosciences).

For metabolomic analysis, a FACS Aria III cell sorter (BD Biosciences) was used to sort immunostained cells into fractions containing immature KLS$^+$ (cKit$^+$Lineage$^-$Sca-1$^+$) cells, progenitor KLS$^-$ (cKit$^+$Lineage$^-$Sca-1$^-$) cells and differentiated Lin$^+$ (Lineage$^+$) cells according to a published classification system. For next-generation RNA sequencing and Duolink® in situ PLA analysis, KLS$^+$ cells were purified into the most primitive long-term (LT) cancer stem cells (CD150$^+$CD48$^-$CD135$^-$KLS$^+$), short-term (ST) cancer stem cells (CD150$^-$CD48$^-$CD135$^-$KLS$^+$), CD48$^+$ cells (CD48$^+$CD135$^-$KLS$^+$) and multipotent progenitor-like (MPP) cells (CD135$^+$KLS$^+$).

For serial transplantation of CML cancer stem cells, GFP/BCR$^-$ABL1$^+$CML KLS$^+$ cells were purified from BM MNCs of BCR-ABL1 CML-affected mice. For retroviral and lentiviral transductions, GFP/BCR$^-$ABL1$^+$CML KLS$^+$ cells and GFP/BCR$^-$ABL1$^+$CML KLS$^-$ were purified from BM MNCs of BCR$^-$ABL1 CML-affected mice. For HSC-competitive reconstitution assays, normal KLS$^+$ cells were purified from BM MNCs of C57BL6 congenic (CD45.1) mice.

3. Metabolomics

For metabolomic profiling, 1.8-2.5×10$^5$ immature KLS$^+$ hematopoietic stem cells, KLS-progenitor cells and Lin$^+$ differentiated cells were isolated from CML-affected Tal1-tTA$^+$ TRE-BCR-ABL1$^+$ mice (n=4 mice in each of the three independent experiments) and normal healthy littermate control (Tal1-tTA$^+$) mice (n=6 mice in each of the two independent experiments) at 5 weeks after doxycycline withdrawal. Metabolites were also determined in 1.0-1.8×10$^5$ immature KLS$^+$ cells isolated from 8-week and 24-week-old C57BL/6 mice (n=6 mice in each of the two independent experiments).

To detect inhibition of dipeptide uptake in vivo, immature KLS$^+$ cells were isolated from tet-inducible CML-affected (Tal1-tTA$^+$TRE-BCR-ABL1$^+$) mice (n=4 mice in each of the three independent experiments), and normal healthy littermate (Tal1-tTA$^+$) mice (n=6 mice in each of the two independent experiments) that had received vehicle or cefadroxil (36 mgKg$^{-1}$day$^{-1}$) by oral gavage for 30 days. For IM administration in vivo, immature KLS$^+$ cells were isolated from normal healthy littermate mice (n=6 mice in each of the two independent experiments) and CML-affected mice (n=4 mice in each of the three independent experiments) that had received vehicle or cefadroxil (36 mgKg$^{-1}$day$^{-1}$). For inhibition of protein degradation/turnover in vitro, CML-KLS$^+$ cells derived from CML-affected mice (n=8 mice in each of the three independent experiments) were plated in serum-free SF-03 stem cell medium (Sanko Junyaku) under hypoxic (3% $O_2$) conditions and treated them for 2 hrs with vehicle, 100 nM Bortezomib (Cell Signaling, #2204) or 100 nM Bafilomycin A1 (Sigma, B1793). In all cases, isolated cell pellets were frozen at −80° C. immediately after obtaining.

Metabolomic profiling was performed by Metabolon Inc. (Durham, N.C.) using ultrahigh-performance liquid chromatography/mass spectroscopy (UPLC/MS/MS) and gas chromatography/MS (GC/MS). Data were compiled using the Metabolon LIMS (Laboratory Information Management System). The UPLC/MS/MS portion of the platform was based on a Waters Acquity UPLC (Waters) and a Q-Exactive high-resolution/accurate mass spectrometer (Thermo Scientific) interfaced with a heated electrospray ionization (HESI-II) source and Orbitrap mass analyzer. GC/MS was performed by a Trace DSQ fast-scanning single-quadrupole mass spectrometer using electron impact ionization (Thermo-Finnigan).

4. Next-Generation RNA Sequencing

LT-cancer stem cells, ST-cancer stem cells, and KLS⁻ progenitor cells isolated from total normal hematopoietic cells and CML cells were directly sorted into 200 µl Isogene (Nippon Gene) solution. RNA extraction and sequencing were performed by Hokkaido System Science Co. Ltd (Sapporo, Japan). RNA quality was confirmed using Nanodrop (Thermo Fisher Scientific) and an Agilent 2100 Bioanalyzer (Agilent Technologies). All RNA samples had an RNA integrity number of >8.5 and exceeded the quality threshold for RNA sequencing. Libraries were constructed from total RNA using a SMARTer Ultra Low Input RNA kit for Illumina Sequencing (Takara Clontech). RNA was fragmented and converted into single-strand cDNA using oligo-dT priming. Paired-end reads of 100 bases were generated using HiSeq2000 (Illumina). Sequence reads in FastQ format were assessed for quality using FastQC. Sequences were mapped to a mouse genome reference (*Mus musculus*; mm9, NCBI Build 37) using SeqNova CS by DNAnexus Inc. (Mountain View, Calif.) (https://dnanexus.com/).

5. Quantitative Real-Time RT-PCR Analysis

Using an RNeasy kit (Qiagen), RNA samples were purified from 4-5×10⁴ LT-stem cells, ST-stem cells, $CD48^+KLS^+$ cells, MPP and KLS⁻ progenitor cells isolated from six tet-inducible CML-affected ($Tal1$-$tTA^+TRE$-$BCR$-$ABL1^+$) mice and eight littermate control ($Tal1$-$tTA^+$) mice at 5 weeks post DOX withdrawal. RNA samples were reverse transcribed using an Advantage RT-for-PCR kit (Takara Clontech). Real-time quantitative PCR was performed using SYBR green Premix EX Taq (Takara) on an Mx3000P® Real-time PCR system (Stratagene).

6. Analysis of Slc15A2 Transporter Activity by [3H] GlySar Uptake

Slc15A2 transporter activity was determined using a well-established assay measuring [3H]GlySar uptake by cells suspended in an acidic transport medium (pH 6.0). Briefly, normal KLS⁺ cells or CML KLS⁺ cells (1×10⁵) were suspended in a transport medium (125 mM NaCl, 4.8 mM KCl, 5.6 mM D-glucose, 1.2 mM $CaCl_2$-$2H_2O_4$, 1.2 mM $KH_2PO_4$, 1.2 mM $MgSO_4$-$7H_2O$ and 25 mM MES, pH 6.0) in the absence or presence of 100 µM cefadroxil (Sigma-Aldrich). To initiate the transporter reaction, [3H]GlySar (Moravek Biochemicals, Brea, Calif.) was added to the cell suspension. After 60 or 120 min, the radioactivity of [3H] GlySar internalized by cells was measured using a liquid scintillation counter.

7. cDNA Construction and Retrovirus Preparation

Retroviral expression vectors encoding human Smad3-wild type (WT), Smad3-3SA (Ser422, Ser423 and Ser425 all converted to Ala) and Smad3-S208A (Ser208 converted to Ala) were constructed using human WT Smad3 cDNA (kindly provided by Dr. Anita B. Roberts, NCI, NIH, Bethesda, Md.) as a template. Briefly, cDNAs encoding the Smad3 3SA and S208A mutants were constructed in pCR2-TOPO vector (Invitrogen) using a High-Fidelity DNA polymerase KOD Plus 2 kit (Toyobo) or a QuikChange site-directed mutagenesis kit (Stratagene). DNA sequences were confirmed by Operon Biotechnology (Tokyo, Japan) using an ABI-3730xl instrument (Applied Biosystems).

EcoRI/XhoI-digested cDNA fragments were inserted into the retroviral expression vector MSCV-ires-GFP. Retroviral packaging cells (Plat-E) were transiently transfected with control GFP vector (MSCV-ires-GFP) or with MSCV-ires-GFP-Smad3 WT, MSCV-ires-GFP-Smad3 3SA, or MSCV-ires-GFP-Smad3 S208A plasmids using FuGene6 (Roche). At 2 days post transfection, culture supernatants were passed through a 0.45-µm filter and centrifuged at 6,500×g for 16 hrs. The virus-containing pellets were resuspended in serum-free SF-03 stem cell medium (Sanko Junyaku) containing 0.1% BSA (#09300; Stem Cell Technology) and penicillin/streptomycin (Gibco), yielding retroviral solutions used for KLS⁺ cell infection.

8. Retroviral Infection of KLS⁺ Cells and Mouse Transplantation

KLS⁺ CML-initiating cells were purified from BM MNCs obtained from the two hindlimbs of tetracycline-inducible CML-affected mice. These cells were cultured overnight in a 3% $O_2$ incubator at 37° C. in 96-well plates containing 200 µl of stem cell medium supplemented with 100 ng/ml human thrombopoietin (TPO, PeproTech) and 100 ng/ml mouse stem cell factor (SCF, Wako Pure Chemical). The next day, these cells were transferred to 96-well plates pre-treated with retronectin (Takara Bio) and incubated for 30 min with 150 µl of the retroviral solutions described above using Combimag (OZ Biosciences) on a magnetic plate (OZ Biosciences). The top half of the supernatant was carefully removed and the infected cells received an additional 100 µl of fresh stem cell medium supplemented with TPO and SCF. Infected cells were cultured overnight in a 3% $O_2$ incubator at 37° C. Retrovirally infected CML-initiating cells (about 1.0-1.5×10⁵ cells/mouse) were injected intravenously into lethally irradiated (9.0 Gy) FVB recipient congenic mice.

9. LT-CML Stem Cell Maintenance In Vivo

In vivo maintenance of LT-CML cancer stem cells in recipient mice was evaluated at 30 days post transplantation. Total MNCs isolated from BM of transplant recipients were immunostained with anti-Sca-1 (E13-161.7)-PE, anti-CD4 (L3T4)-biotin, anti-CD8 (53-6.7)-biotin, anti-B220 (RA3-6B2)-biotin, anti-TER119 (Ly-76)-biotin, anti-Gr-1 (RB6-8C5)-biotin, anti-Mac1 (M1/70)-biotin antibodies (all purchased from BD Biosciences); anti-CD135/Flk2/Flt3 (A2F10)-biotin and anti-c-Kit (ACK2)-APC antibodies (both purchased from eBiosciences); and anti-CD48 (HM48-1)-APC-Cy7 and anti-CD150/SLAM (TC15-12F12.2)-Pacific blue (both purchased from BioLegend). Biotinylated primary antibodies were visualized with Streptavidin-PE-Cy7 (BD Biosciences).

The frequency of GFP (Smad3)+ LT-CML stem cells among total GFP (Smad3)+KLS+CML-initiating cells was determined using a FACS Aria III cell sorter (BD Biosciences).

10. Duolink® In Situ Proximity Ligation Assay (PLA)

To examine phosphorylation of Smad2, Smad3, p38MAPK, AMPK, and S6 ribosomal protein, and Foxo3a-Smad2 and Foxo3a-Smad3 interactions, Duolink® in situ PLA assay (Olink Bioscience) was used. LT-CML stem cells, ST-CML stem cells, CD48+, MPP, and KLS− CML cells that were freshly isolated from CML-affected mice, and LT-normal HSCs that were freshly isolated from healthy control littermates, were immediately fixed with 4% paraformaldehyde for 30 min.

For in vitro inhibitor experiments, LT-CML stem cells were incubated in 3% $O_2$ at 37° C. for 30 min with vehicle (control; artificial gastric fluid solution (900 ml dd$H_2O$ containing 2.0 g of NaCl, 7 ml of conc. HCl and 3.2 g of pepsin)), 5 µM Ly364947 (TGF-β type I receptor kinase Alk5 inhibitor; Merck), 5 µM SB203580 (p38MAPK inhibitor; LC Laboratories), 5 µM GlySar (dipeptide transporter inhibitor; Sigma-Aldrich), 5 µM cefadroxil (dipeptide transporter inhibitor; Sigma-Aldrich), or 100 nM rapamycin (mTORC1 inhibitor; Cell Signaling Technologies). Treated cells were fixed with 4% paraformaldehyde for 30 min, and treated with 0.25% Triton X-100 for 15 min, washed and blocked by incubation in 5% FBS in TBS for 1 hr.

Figure 8A:
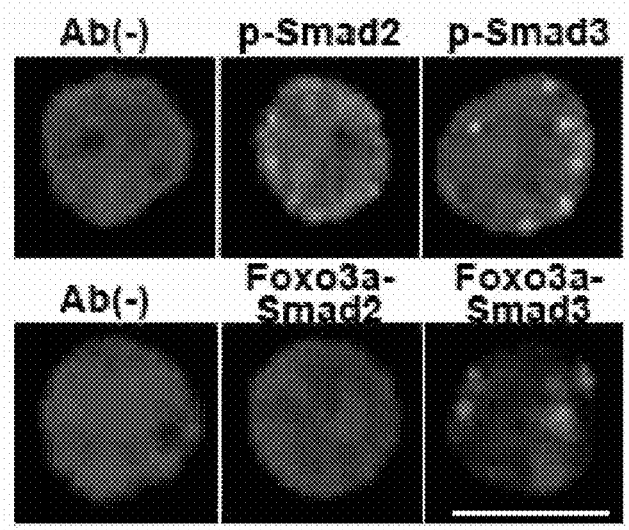
FIGS. 8 to 12 show that non-canonical Smad3 Ser208 phosphorylation supports LT-CML stem cells in vivo.
Figure 8B:
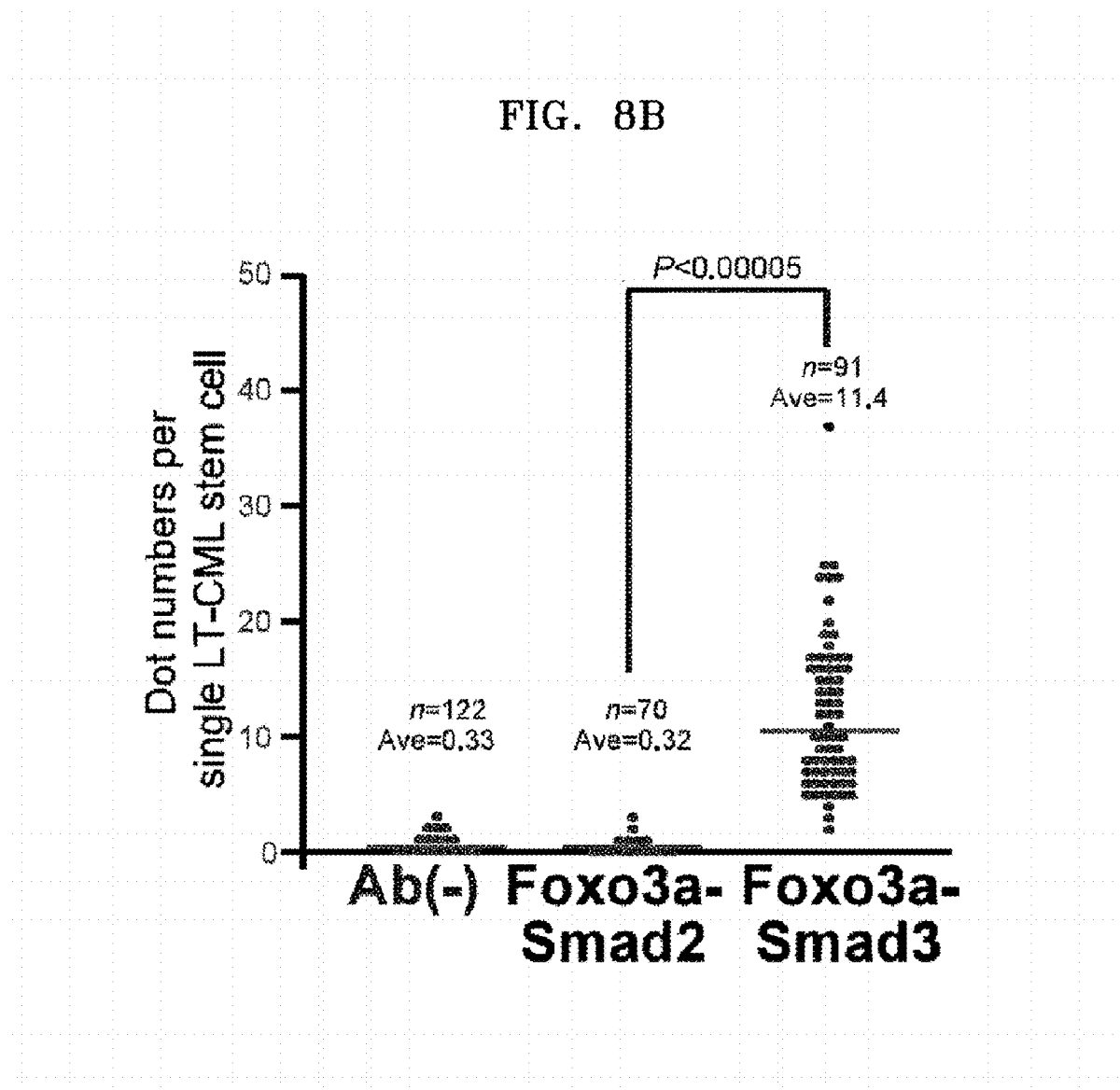
Figure 9A:
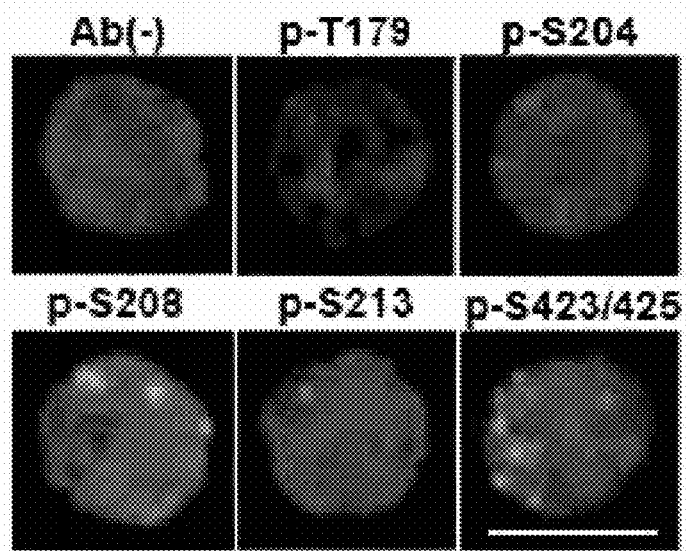
Figure 9B:
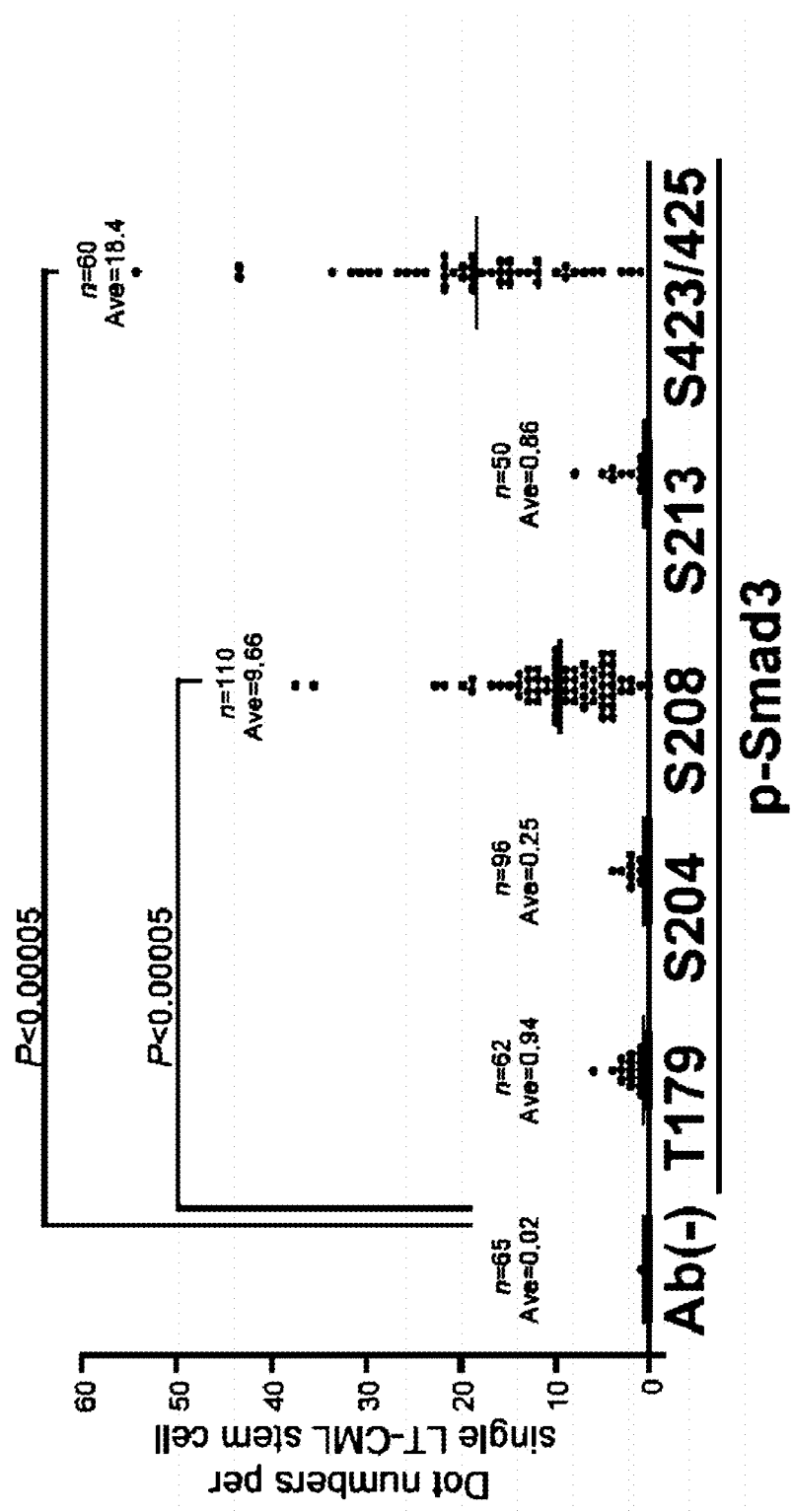

Blocked cells were incubated overnight at 4° C. with the combinations of antibodies indicated in the following Table 1. The proximate binding of these antibodies was then detected using Duolink® in situ PLA system which employs a set of two secondary antibodies in which one is conjugated to a minus strand PLA probe and the other is conjugated to a plus strand PLA probe. Nuclei were stained with DNA marker DAPI (Sigma). Stained slides were mounted using Fluoromount Plus (Diagnostic Biosystems) and fluorescent images were acquired by confocal microscopy (FV10i, Olympus) and Photoshop software (Adobe). The number of fluorescent foci per single cell was quantified using Duolink®Image Tool software (Olink Bioscience).

antibody and confirmed that no fluorescent foci could be detected, as shown in FIGS. 8 and 9.

11. Colony-forming Assays

LT-CML stem cells or LT-normal HSCs ($1 \times 10^3$/plate) were co-cultured on OP-9 stromal cells for 5 days in the presence of either vehicle (control) or a dipeptide transporter inhibitor cefadroxil (5 µM). Cells were harvested, washed with PBS, and plated in semi-solid methylcellulose medium containing SCF, IL-3, IL-6 and erythropoietin (Methocult GF M3434; Stem Cell Technologies). After growth for 7 days in a humidified atmosphere containing 5% $CO_2$ at 37° C., colony numbers were counted under a light microscope.

For combination treatments of dipeptide transporter inhibitor+tyrosine kinase inhibitor (TKI), LT-CML cancer stem cells ($3 \times 10^3$) were plated on OP-9 stromal cells in the presence of cefadroxil (5 µM). After 24 h in culture, the cells received additional DMSO or 1 µM IM (Axon Medchem) and were incubated for another 4 days (total 5 days). Treated cells were washed with PBS, transferred to a semi-solid medium, and colony formation after 7 days was assessed as described above.

12. Short Hairpin (Sh) RNA Targeting Slc15A2 mRNA

Third-generation HuSH shRNA lentiviral vectors based on pGFP-C-shLenti and carrying 29-mer shRNA sequences targeting mouse Slc15A2 gene (mouse Slc15A2 shB: 5'-GAA CCG TTC TGA GGA CAT TCC AAA GCG AC-3' mouse Slc15A2 shD: 5'-TAT CGG CTG ATC TCC AAG TGC GGA GTT AA-3') and control scrambled shRNA were purchased from Origene (Rockville, Md.). pCMV-VSV-G and pCMV-dR8.2 dvpr were provided by Addgene (Cambridge, Mass.). 293TN producer cells (System Biosciences;

TABLE 1

| Purpose | Detection | PLA plus strand | PLA minus strand |
| --- | --- | --- | --- |
| Phosphorylation | p-Ser465/467 Smad2 | Goat anti-phospho-Ser465/467 Smad2/ phospho-Ser423/425 Smad3 (Santacruz, Sc-11769) | Rabbit anti-Smad2 (D43B4) (Cell Signaling, #5339) |
| | p-Thr179 Smad3 | Rabbit anti-Smad3 (C67H9) (Cell Signaling, #9523) | Mouse anti-phospho-Thr179 Smad3/ phospho-Thr220 Smad2 (IBL, 1A1) |
| | p-Ser204 Smad3 | Rabbit anti-phospho-Ser204 Smad3 (Abcam, ab63402) | Mouse anti-Smad3 (Abcam, ab75512) |
| | p-Ser208 Smad3 | Rabbit anti-phospho-Ser208 Smad3 (Abcam, ab138659) | Mouse anti-Smad3 (Abcam, ab75512) |
| | p-Ser213 Smad3 | Rabbit anti-phospho-Ser213 Smad3 (Millipore, ABS48) | Mouse anti-Smad3 (Abcam, ab75512) |
| | p-Ser423/425 Smad3 | Rabbit anti-phospho-Ser423/425 Smad3 (Abcam, ab51451) | Mouse anti-Smad3 (Abcam, ab75512) |
| | p-Thr180/Tyr182 p38MAPK | Rabbit anti-p38MAPK (Cell Signaling, D13E1 #8690) | Mouse anti-phospho-Thr180/Tyr182 p38MAPK (Cell Signaling, 28D10 #9216) |
| | p-Thr172 AMPK | Rabbit anti-phospho-Thr172 AMPK (40H9) (Cell Signaling, #2535) | Mouse anti-AMPKα (F6) (Cell Signaling, #2793) |
| | p-Ser235/236 S6 ribosomal protein | Rabbit anti-phospho-Ser235/236 S6 ribosomal protein (D57.2.2E) (Cell Signaling, #4858) | Mouse anti-S6 ribosomal protein (54D2) (Cell Signaling, #2317) |
| Interaction | Smad2-Foxo3a | Rabbit anti-Smad2 (D43B4) (Cell Signaling, #5339) | Mouse anti-FKHRL1(FR1) (Sigma, F1304) |
| | Foxo3a-Smad3 | Rabbit anti-Foxo3a (75D8) (Cell Signaling, #2497) | Mouse anti-Smad3 (Abcam, ab75512) |

As positive and negative controls for Smad3 phosphorylation, LT-CML cancer stem cells were treated in vitro with TGF-β1 (1 ng/ml; R&D Systems) or Ly364947 (5 µM; Merck), respectively, and incubated for 30 min in 3% $O_2$. As a negative control for mTORC1 activation, LT-CML cancer stem cells were treated in vitro with rapamycin (100 nM; Cell Signaling Technologies), and incubated. As shown in FIG. 3 and FIGS. 13 to 15, the appropriate fluorescent foci were detected (or not) in these control experiments. As a technical negative control for D-PLA, LT-CML cancer stem cells were treated in vitro with a single anti-mouse primary Mountain View, Calif.) were transiently transfected with pGFP-C-shLenti vector (6 µg per 100 mm plate), pCMV-VSV-G (1.5 µg) and pCMV-dR8.2 dvpr (4.5 µg) using FuGene6 (Roche) as described above for retroviral transduction of KLS+ cells. At 2 days post transfection, culture supernatants were filtered with a 0.45-µm filter and centrifuged at 6,500×g for 16 hrs. The virus-containing pellets were resuspended in stem cell medium to yield lentiviral solutions carrying shRNA targeting mouse Slc15A2 mRNA or scrambled shRNA. CML-KLS+ cells and CML-KLS− cells isolated from tet-inducible CML-affected mice were infected with the lentiviruses, and GFP+CML-KLS+ and GFP+CML-KLS− cells were isolated by cell sorting at 3 days post infection. To examine colony-forming ability in vitro, these cells were co-cultured on OP-9 stromal cells under hypoxic conditions (3% $O_2$) for 5 days, and colony formation was assessed as described above.

13. Competitive Reconstitution Assay for Normal HSCs

C57BL/6 (CD45.2 for the Ly5 locus) and congenic C57BL/6 (CD45.1 for the Ly5 locus; B6-Ly5.1) mice were purchased from Sankyo-Lab Service (Tsukuba, Japan). Lethally irradiated (9 Gy) C57BL/6 (CD45.2) recipient mice were reconstituted with $1\times10^4$ normal KLS+ cells (HSCs) from congenic C57BL/6 (CD45.1) (B6-Ly5.1) mice in competition with $5\times10^5$ unfractionated BM MNCs derived from C57BL/6 (CD45.2) mice. Transplanted recipients then received vehicle or cefadroxil (36 $mgKg^{-1}day^{-1}$) from day 0 to 8 weeks post transplantation. Reconstitution of donor-derived cells (CD45.1) was monitored at 4 and 8 weeks post transplantation by flow cytometric analysis of peripheral blood mononuclear cells stained with monoclonal antibodies (mAbs) against CD45.2 (104)-FITC and CD45.1 (A20)-PE.

14. Serial Transplantation of CML Stem Cells

To evaluate the retention of the disease-initiating capacity by CML stem cells after treatment of mice with cefadroxil in vitro and/or IM in vivo, the number of GFP/BCR-ABL1+ CMLKLS+ cells in treated BCR-ABL1 CML-affected mice was determined, and subsequent secondary transplantation of the cells was performed. Briefly, CML-affected mice received by oral gavage for 30 days post BM transplantation as described above. The number of GFP/BCR-ABL1+CML-KLS+ cells among total GFP/BCR-ABL1+CML cells isolated from BM MNCs acquired from the two hindlimbs of treated CML-affected mice was assessed by flow cytometry. Freshly purified GFP/BCR-ABL1+CML-KLS+ cells ($3\times10^4$) were then serially transplanted into a second set of lethally irradiated congenic recipient mice along with $5\times10^5$ normal BM MNCs derived from C57BL/6 mice. Mouse survival and disease recurrence were monitored for 90 days.

15. SLC15A2 mRNA Expression in Human CML Patients

Data on SLC15A2 mRNA levels in human CML patients were obtained from a public database gene expression (GEO, ID: GSE33075) that contains microarray analyses of nine healthy donors, nine CML patients, and the same nine CML patients at 1 month after treatment with IM. A one-sided paired t-test was used to compare SLC15A2 expression between CML patients and after IM treatment. Independent samples were used to compare SLC15A2 expression between CML patients and healthy donors.

16. Colony-forming Capacity of Human CML-Leukemia Initiating Cells

Viable BM MNCs from three human patients with chronic phase CML were purchased from AllCells (#06-255, #06-620, and #147742, Alameda, Calif., USA). Documents confirming the informed consent of the patient are available in http://www.veritastk.co.jp/attached/3978/AllCells_BM_Informed_Consent_Form.pdf. These cells were stained with anti-CD34(8G12), anti-CD38(HIT2), anti-CD3(SK7), anti-CD16(3G8), anti-CD19(SJ25C1), anti-CD20(L27), anti-CD14(MpP9), and anti-CD56(NCAM16.2) antibodies (all purchased from BD Biosciences). A mixture of mAbs recognizing CD3, CD16, CD19, CD20, CD14 and CD56 was used to identify Lin− cells, and CD34+CD38−Lin− cells were purified. To determine the effects of treatment with cefadroxil (5 µM) alone, or with a combination of cefadroxil+IM (1 µM; Axon Medchem) or dasatinib (500 nM; LC laboratories), CD34+CD38−Lin− cells were cultured on OP-9 stromal cells under hypoxic (3% $O_2$) conditions.

After harvesting and washing with PBS, the colony-forming ability of the most primitive human CML leukemia-initiating cells (LICs) was evaluated by culture in semi-solid methylcellulose medium containing SCF, GM-CSF, IL-3, IL-6, G-CSF, and erythropoietin (Methocult GF+ H4435; Stem Cell Technologies). After growth for 7 days at 37° C. under hypoxic (3% $O_2$) conditions, colony numbers were counted under a light microscope.

17. Statistical Analyses

Statistical differences were determined using the unpaired Student's t-test for P values and a log-rank non-parametric test for survival curves. Statistical analysis for metabolomic data was performed by using program "R" (http://cran.r-project.org/).

Example 1

CML Cancer Stem Cells Accumulate Several Dipeptide Species

A nutrient supply required for CML cancer stem cell maintenance may be a candidate target for a novel therapy capable of eradicating CML cancer stem cells. However, to reduce harmful side effects of the candidate target on normal hematopoietic stem cells, it is essential to understand the altered mechanisms that distinguish CML cancer stem cells from normal HSCs. To identify nutrient signaling differences, a global metabolic comparison of normal HSCs with CML cancer stem cells isolated from tetracycline-inducible CML-affected mice was carried out.

To obtain the tetracycline-inducible CML-affected mouse models, Tal1-tTA mice were crossed with TRE-BCR-ABL1 transgenic mice (FVB/N background) to generate Tal1-tTA× TRE-BCR-ABL1 double-transgenic mice. When these progeny are subjected to doxycycline (DOX) withdrawal, synchronous induction of CML disease occurs with the generation of CML cancer stem cells. From healthy control (Tal1-tTA+) and CML-affected mouse (Tal1-tTA+TRE-BCR-ABL1+), cells subsets of immature KLS+ (cKit+Lineage−Sca-1+) population, which includes normal HSCs and CML cancer stem cells (also known as leukaemia-initiating cells (LICs)), the committed progenitor KLS− (cKit+Lineage−Sca-1−) population, and the mature Lin+ (Lineage+) population were isolated.

Complex metabolomic techniques were applied to examine the metabolites of these cells. Although quiescent normal HSCs reportedly produce adenosine 5'-triphosphate (ATP) through anaerobic glycolysis, no differences were observed in levels of glucose, fructose 1,6-bisphosphate (F-1,6-bP), or pyruvate between normal KLS+ cells and CML-KLS+ cells (FIG. 1A). Adenosine 5'-monophosphate (AMP) levels were slightly higher in CML-KLS+ cells than in normal KLS+ cells, but ATP was not measurable in either population. Therefore, both of normal KLS+ cells and CML-KLS+ cells showed a high AMP/ATP ratio indicating relative energy deficient condition (data not shown).

Figure 1B:
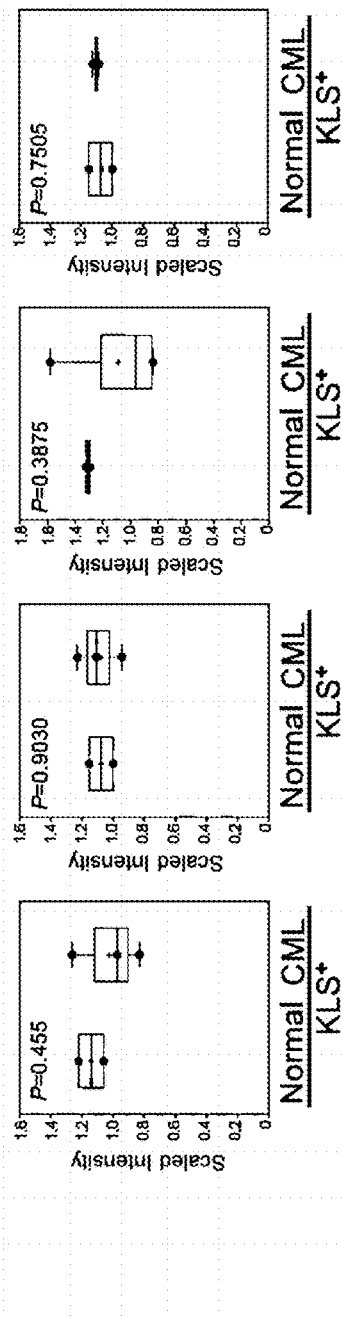
Figure 1C:
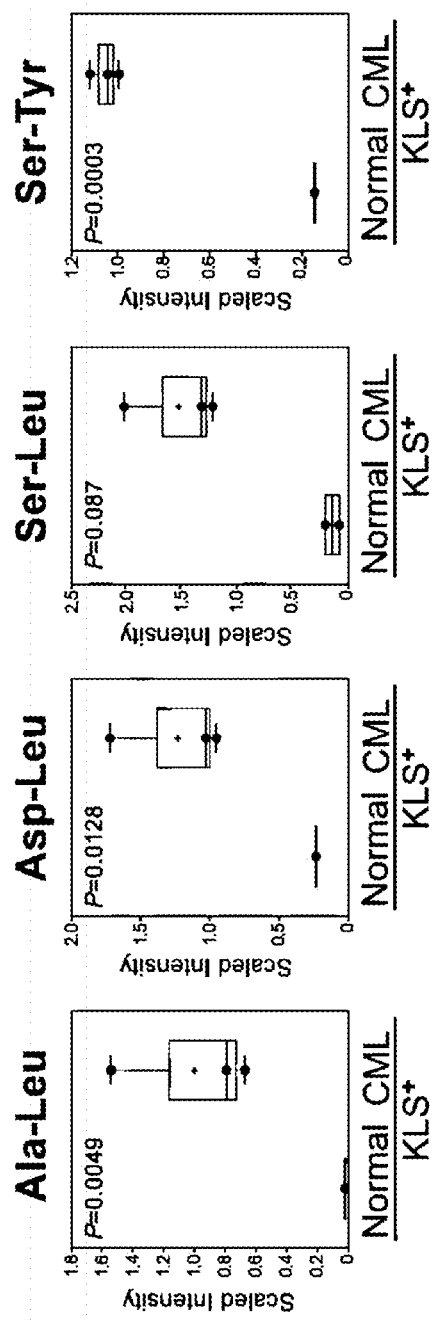

When levels of various individual amino acids were measured, no differences between normal KLS+ and CML-KLS+ cells were observed (FIG. 1B). However, surprisingly, several dipeptide species were markedly increased in CML-KLS+ cells, as compared with normal KLS+ cells isolated from healthy littermate (FVB/N) mice (FIG. 1C) or form 8- or 24-week old healthy C57BL/6 control mice (data not shown). A calculation of the ratio of dipeptide levels in CML cells vs normal cells at each stage indicated that, compared with mature CML cells, it is the immature CML-KLS+ population that tends to have the largest dipeptide content (FIG. 2). While dipeptides were also elevated in the CML-KLS⁻ progenitor population, it is believed that this increase was likely due to the increased protein turnover/degradation that is required to support the proliferation of CML progenitors. Thus, unlike normal HSCs and mature CML cells, CML cancer stem cells store amino acids in dipeptide pools.

Example 2

CML Stem Cells Take Up Dipeptides Via Dipeptide Transporter

Figure 19:
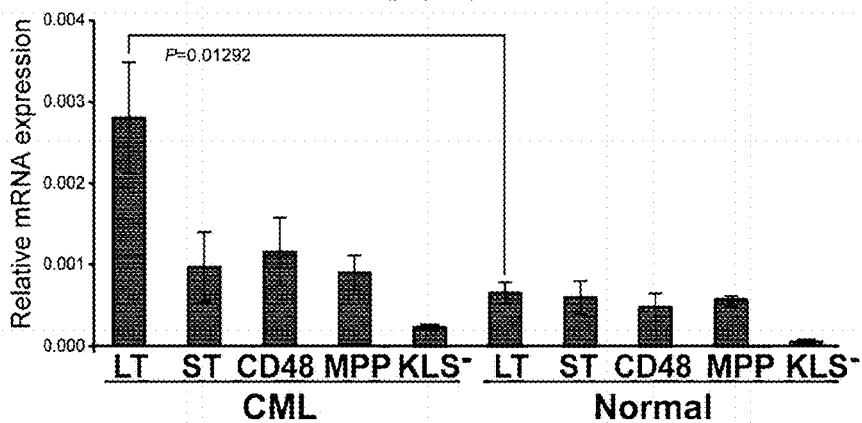
FIG. 19 shows qRT-PCR determination of relative Slc15A2 mRNA levels in LT-stem cells, ST-stem cells, CD48$^+$, MPP, and KLS$^-$ cells from CML-affected (Tal1-tTA$^+$TRE-BCR-ABL1$^+$) mice and normal littermate control (Tal1$^-$tTA) mice at 5 weeks post DOX withdrawal. Data are the mean ratio±s.d. of expression levels normalized to Actb (β-actin) (n=3).

To investigate why dipeptides are accumulated in immature CML cells, upstream gene expression patterns were examined. The most primitive LT-CML cancer stem cells (CD150⁺CD48⁻CD135⁻KLS⁺ cells), ST-stem cells (CD150⁻CD48⁻CD135⁻KLS⁺ cells), and KLS⁻ progenitor cells were isolated from healthy littermate control and CML-affected mice, and gene expression profiling was performed using next-generation RNA sequencing. Genes that were upregulated in LT-CML cancer stem cells but not in CML-KLS⁻ cells or normal LT-HSCs were screened, and 107 such genes were identified. Among them, Slc15A2 gene encoding an oligo-/dipeptide transporter, which quantitative real-time RT-PCR analyses confirmed, was highly expressed in LT-CML cancer stem cells compared with CML-KLS⁻ progenitors and normal LT-HSCs (FIG. 19).

Figure 20:
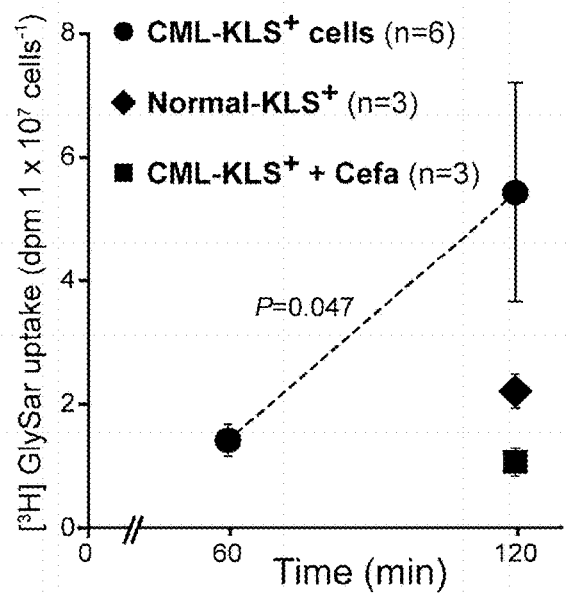
FIG. 20 shows quantification result of dipeptide transporter activity.

To analyze whether Slc15A2 activity was in fact implicated in the dipeptide accumulation observed in Example 1, CML-KLS⁺ cells were incubated in vitro with [3H]-labeled glycylsarcosine([3H]GlySar), which is a dipeptide analogue that cannot be metabolized and acts as a substrate of Slc15A family transporters. As a result, CML-KLS⁺ cells internalized much more [3H]GlySar than normal KLS⁺ cells, and this uptake was markedly decreased in the presence of the Slc15A2-specific chemical inhibitor cefadroxil (FIG. 20).

Figure 21:
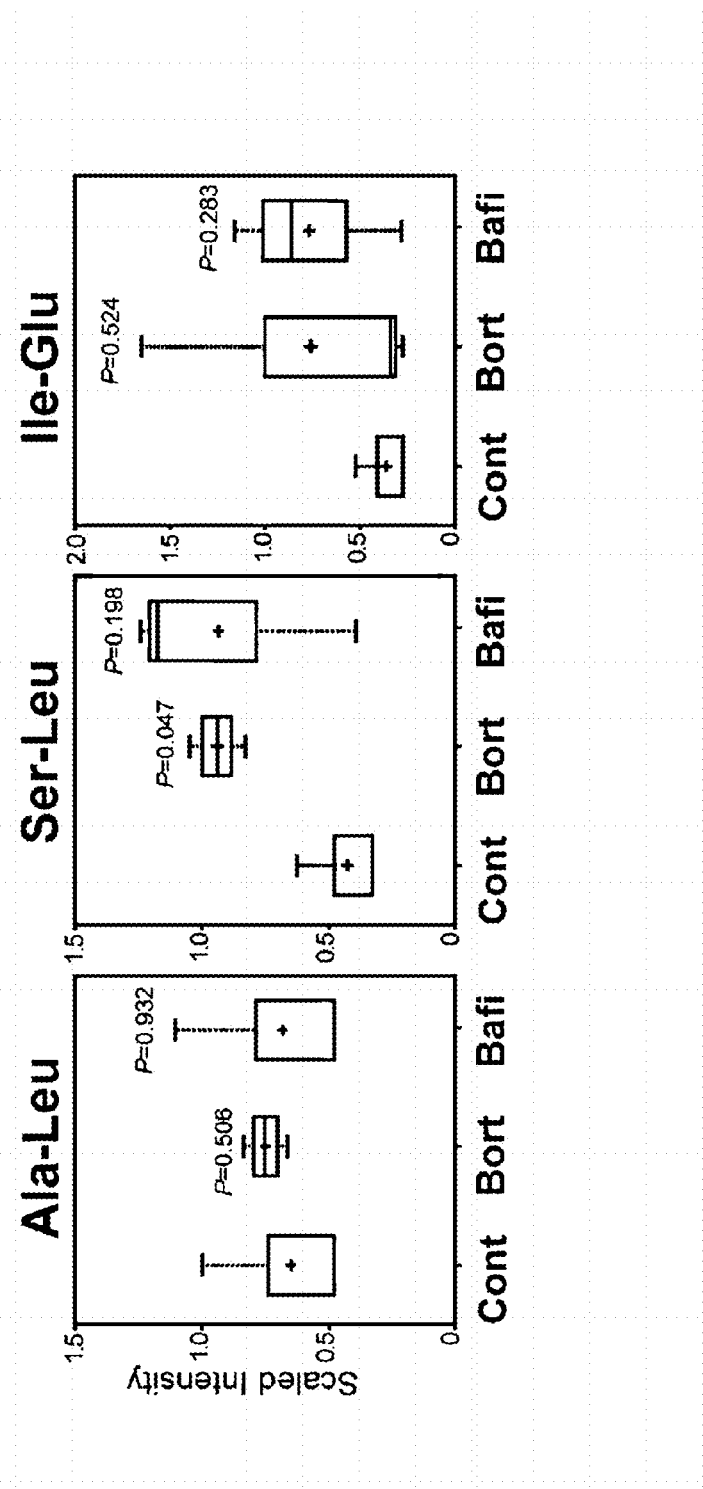
FIG. 21 shows metabolomic analyses of dipeptide species in KLS$^+$ cells which were isolated from CML-affected mice (n=8 in each of three independent experiments) and received bortezomib (Bort; 100 nM) or bafilomycin A1 (Bafi; 100 nM) in vitro for 2 hours.

The possibility that defective protein degradation might contribute to the dipeptide accumulation in CML cancer stem cells was evaluated. Treatment of these cells in vitro with Bortezomib (26S proteasome inhibitor) or Bafilomycin A1 (autophagy inhibitor) decreased individual amino-acid levels, but increased significantly dipeptide accumulation (FIG. 21). Thus, proteasomal degradation or autophagy does not appear to be the major cause of dipeptide accumulation in CML cancer stem cells.

Figure 5:
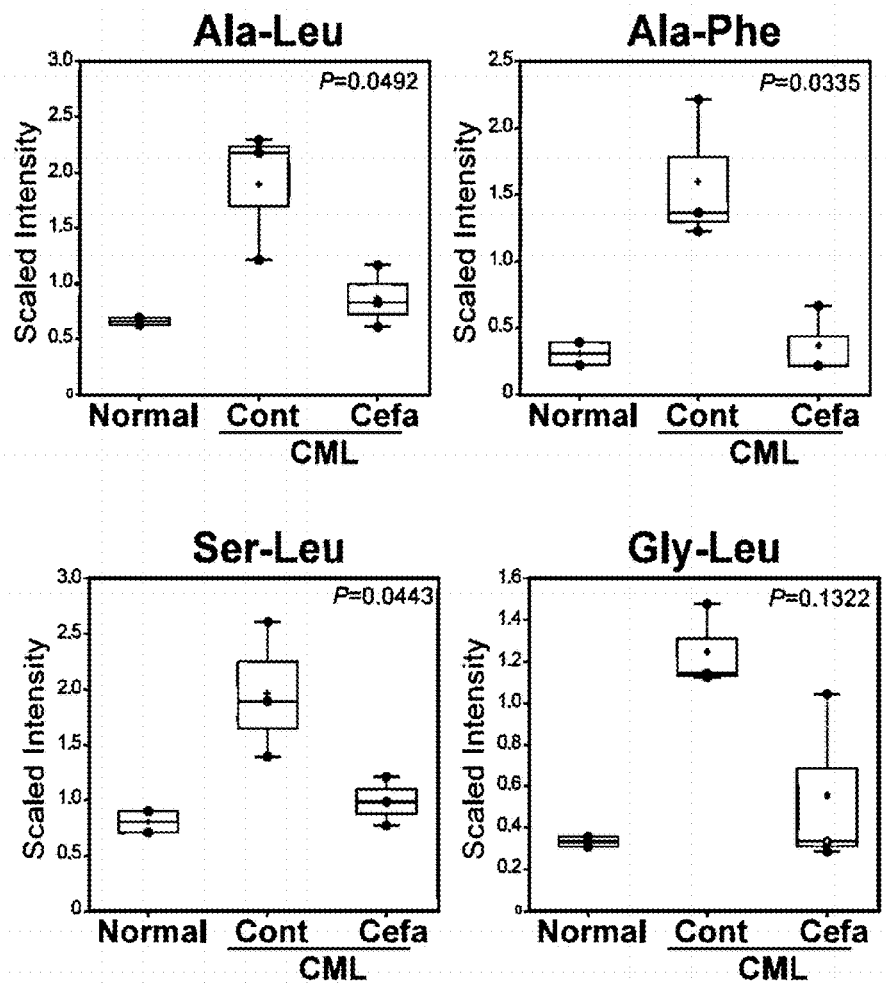

On the basis of the in vitro results, it was examined whether cefadroxil could attenuate dipeptide internalization by CML cancer stem cells in vivo. CML-affected mice received oral administration of cefadroxil for 30 days, followed by metabolomics analysis of CML cancer stem cells to measure intracellular dipeptides. As a result, exposure to cefadroxil decreased levels of several dipeptides in immature CML-KLS⁺ cells, implying impaired uptake of these dipeptide species (FIG. 5). Combined with the in vitro data, these in vivo results implicate Slc15A2 transporter activity as a major driver of dipeptide accumulation in CML cancer stem cells.

Figure 6:
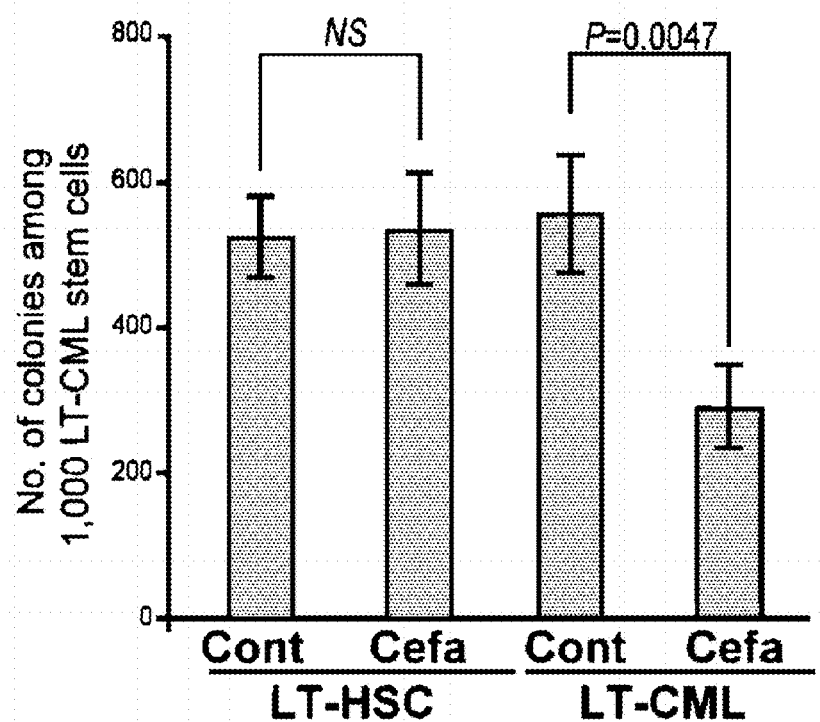
Figure 7A:
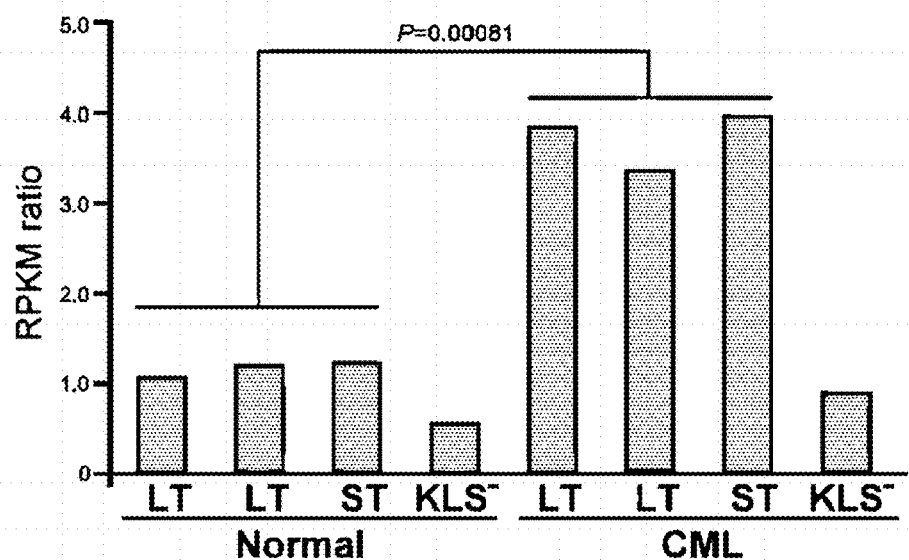
Figure 7B:
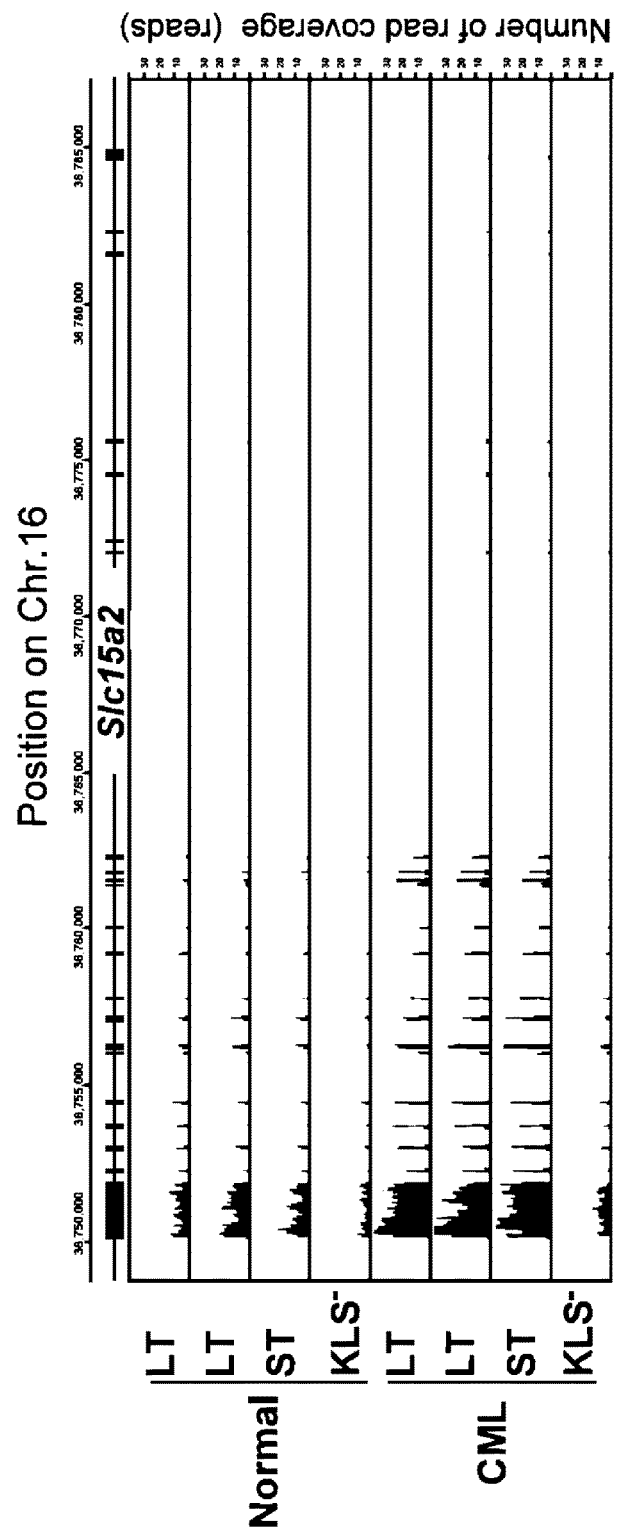
Figure 22:
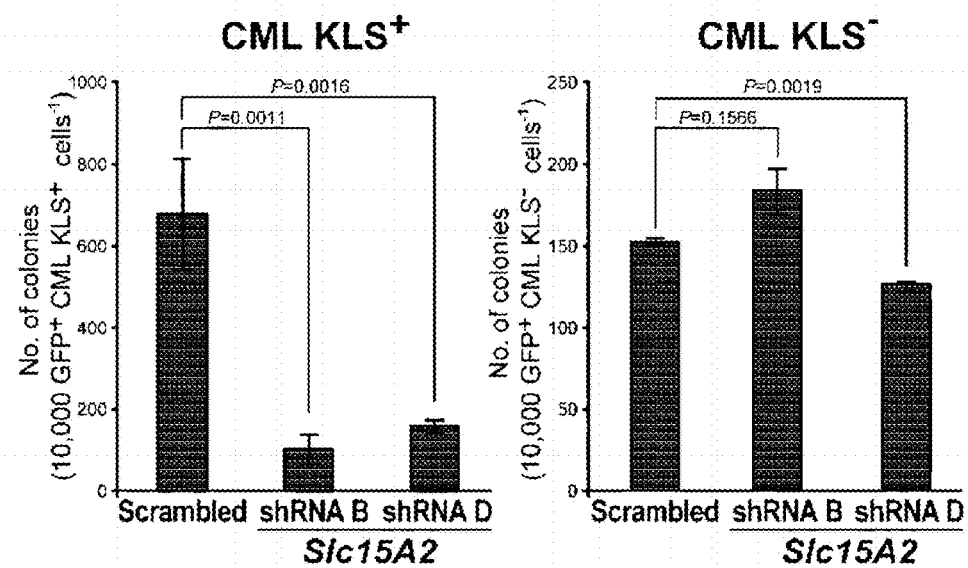
FIG. 22 shows quantification result of colony-forming capacity of CML-KLS$^+$ and CML-KLS$^-$ cells lentivirally transduced to express scrambled shRNA or shRNA targeting Slc15A2.

To understand the biological role of dipeptide uptake in CML cancer stem cells, it was evaluated how inhibition of dipeptide transporter function affected CML cancer stem cell activity in vitro. Treatment with cefadroxil significantly decreased the colony-forming capacity of LT-CML cancer stem cells whereas cefadroxil-treated HSCs maintained normal levels of colony-forming capacity (FIG. 6). Lentiviral transduction of short hairpin RNAs (shRNAs) targeting Slc15A2 mRNA also decreased the colony-forming capacity of CML-KLS⁺ cells but not that of CML-KLS⁻ cells (FIG. 22). These data suggest that dipeptide uptake through the Slc15A2 dipeptide transporter maintains survival of CML cancer stem cell in vitro.

Figure 3:
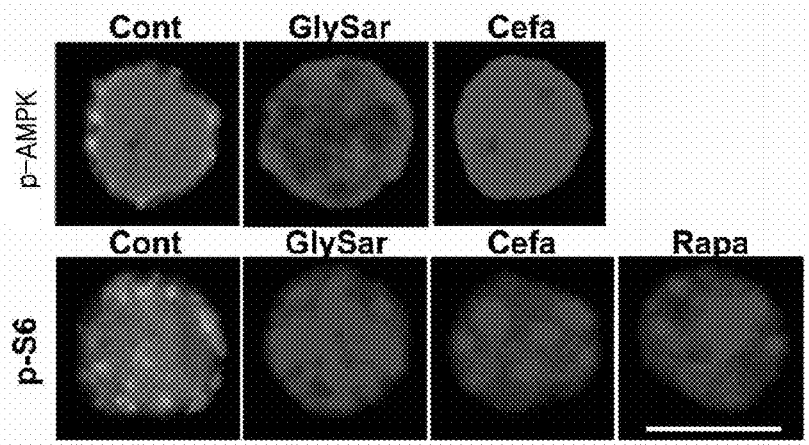
FIGS. 3 to 7 show that CML cancer stem cells internalize dipeptides via dipeptide transporters.
Figure 4:
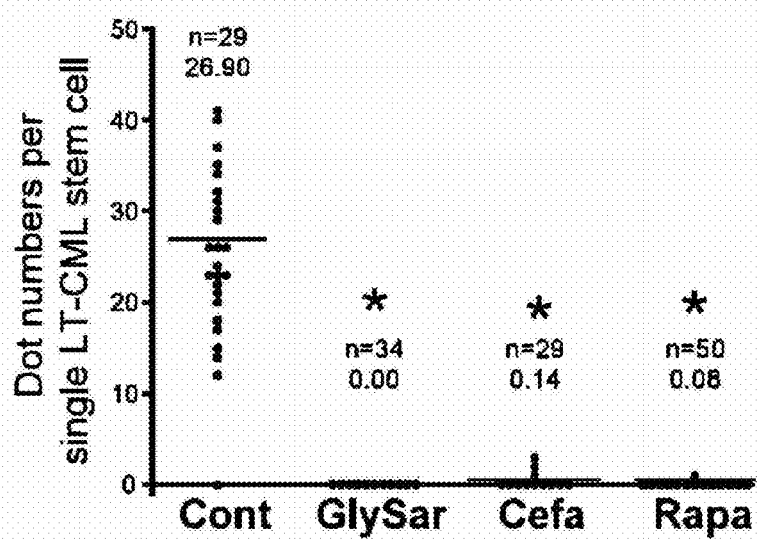

Next, the effect of inhibited dipeptide uptake on self-renewal capacity of LT-CML cancer stem cells was examined by comparing with normal HSCs in vitro. To identify the pathway mediating intracellular nutrient signaling associated with dipeptide uptake, it was first investigated whether treatment in vitro of LT-CML cancer stem cells with GlySar or cefadroxil affected signaling via the mTORC1 pathway. LT-CML were exposed to 5 μM GlySar or cefadroxil for 30 min and highly sensitive Duolink® in situ proximity ligation assay (D-PLA) was used to examine phosphorylation of Raptor-Ser863 and S6 ribosomal protein. As expected, it was found that untreated control LT-CML cancer stem cells exhibited both phospho-Raptor-Ser863 and phospho-S6 (FIG. 3). However, after treatment with GlySar or cefadroxil, LT-CML cancer stem cells displayed decreased phosphorylation of Raptor-Ser863 and S6, similar to the treatment result of rapamycin which is a mTORC1 inhibitor (FIGS. 3-4). These results indicate that interference with Slc15A2-mediated dipeptide uptake, either by a competitive or chemical inhibitor, attenuates mTORC1-mediated nutrient signaling in LT-CML cancer stem cells.

AMPK becomes phosphorylated in cells experiencing low energy or nutrient starvation conditions, leading to suppression of downstream mTORC1 pathway. Treatment of LT-CML cancer stem cells with Metformin, which is a known activator of AMPK, increases the phosphorylation of both AMPK and Raptor-Ser792, and phospho-Raptor-Ser792 suppresses mTORC1 activity. However, although treatment of LT-CML cancer stem cells with GlySar or cefadroxil increased phospho-AMPK, these agents did not promote Raptor-Ser792 phosphorylation. Thus, AMPK pathway is dispensable for the suppression of the mTORC1 pathway seen in LT-CML cancer stem cells experiencing inhibition of Slc15A2-mediated dipeptide uptake.

Example 3

Smad3-Ser208 Phosphorylation Supports LT-CML Cancer Stem Cells

Although it was found that dipeptides were able to influence nutrient signaling via the mTORC1 pathway (see FIGS. 3 and 4), it has been reported that rapamycin treatment does not prolong the survival of CML-affected mice, suggesting that mTORC1 signaling is not crucial for the maintenance of CML stem cells in vivo. Because TGF-β-FOXO-BCL6 signaling pathway is essential for CML cancer stem cell maintenance in vivo, it was examined that there might be a connection between this axis and dipeptide-mediated nutrient signaling that could promote CML cancer stem cell activity in vivo. To identify the key molecule responsible for the potential cross-talk between nutrient signaling and TGF-β-FOXO-BCL6 axis, and thereby for CML stemness, it was investigated whether Smad2/3, which is the downstream effectors of TGF-β signaling, were implicated in nutrient signaling in CML cancer stem cells. As a result, it was found that both Smad2 and Smad3 were phosphorylated at the relevant C-terminal sites. However, D-PLA analysis of LT-CML cancer stem cells revealed that only Smad3 interacted with Foxo3a, consistent with a previous report (FIG. 8). These results suggested that Smad3 might be involved in the TGF-β-FOXO signaling cascade responsible for CML cancer stem cell maintenance.

Figure 10A:
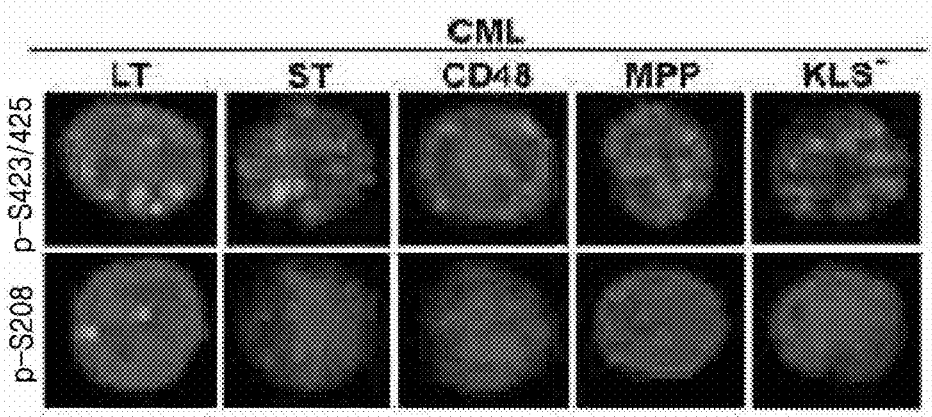
Figure 10B:
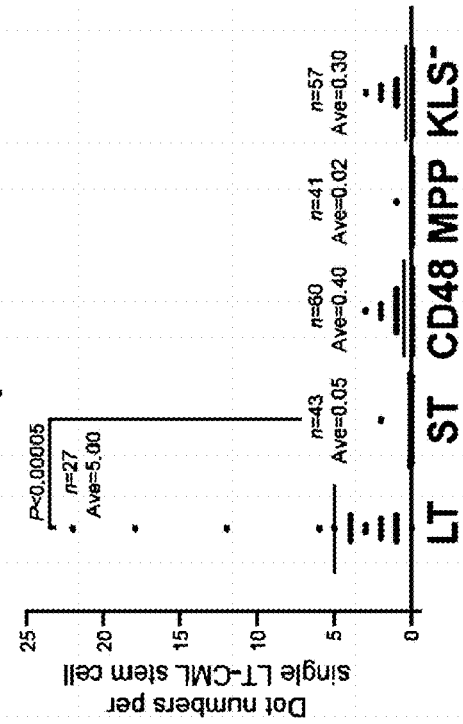
Figure 10B:
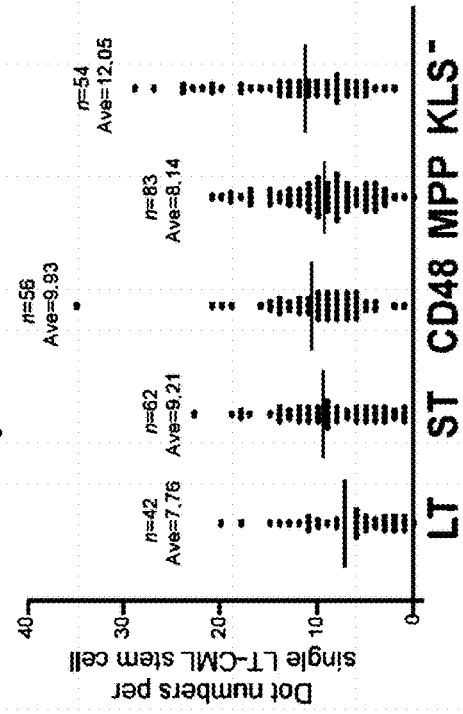

Because Smad3 is a known stemness transcription factor, it has been of interest to determine whether Smad3 promotes the maintenance of CML cancer cell stemness. Therefore, Smad3 phosphorylation sites were examined in TGF-β-treated and control LT-CML cancer stem cells. Whereas D-PLA detected total phosphorylation of Smad3 at Thr179, Ser204, Ser208, Ser213 and Ser423/425 residues in TGF-β-treated LT-CML stem cells, freshly purified LT-CML cancer stem cells showed Smad3 phosphorylation only at Ser423/425 and Ser208 (FIG. 9). Interestingly, although Smad3 Ser423/425 was also phosphorylated in ST-CML cancer stem cells and in $CD48^+$, MPP ($CD135^+KLS^+$) and KLS-CML cells, Smad3-Ser208 phosphorylation was unique to the most primitive LT-CML cancer stem cells, as was Smad3-Foxo3a interaction (FIG. 10). These data suggest that phosphorylation of Smad3 at Ser208 may allow LT-CML stem cells to activate Foxo3a, whose transcriptional activity supports CML cancer stem cell maintenance in vivo.

Figure 11:
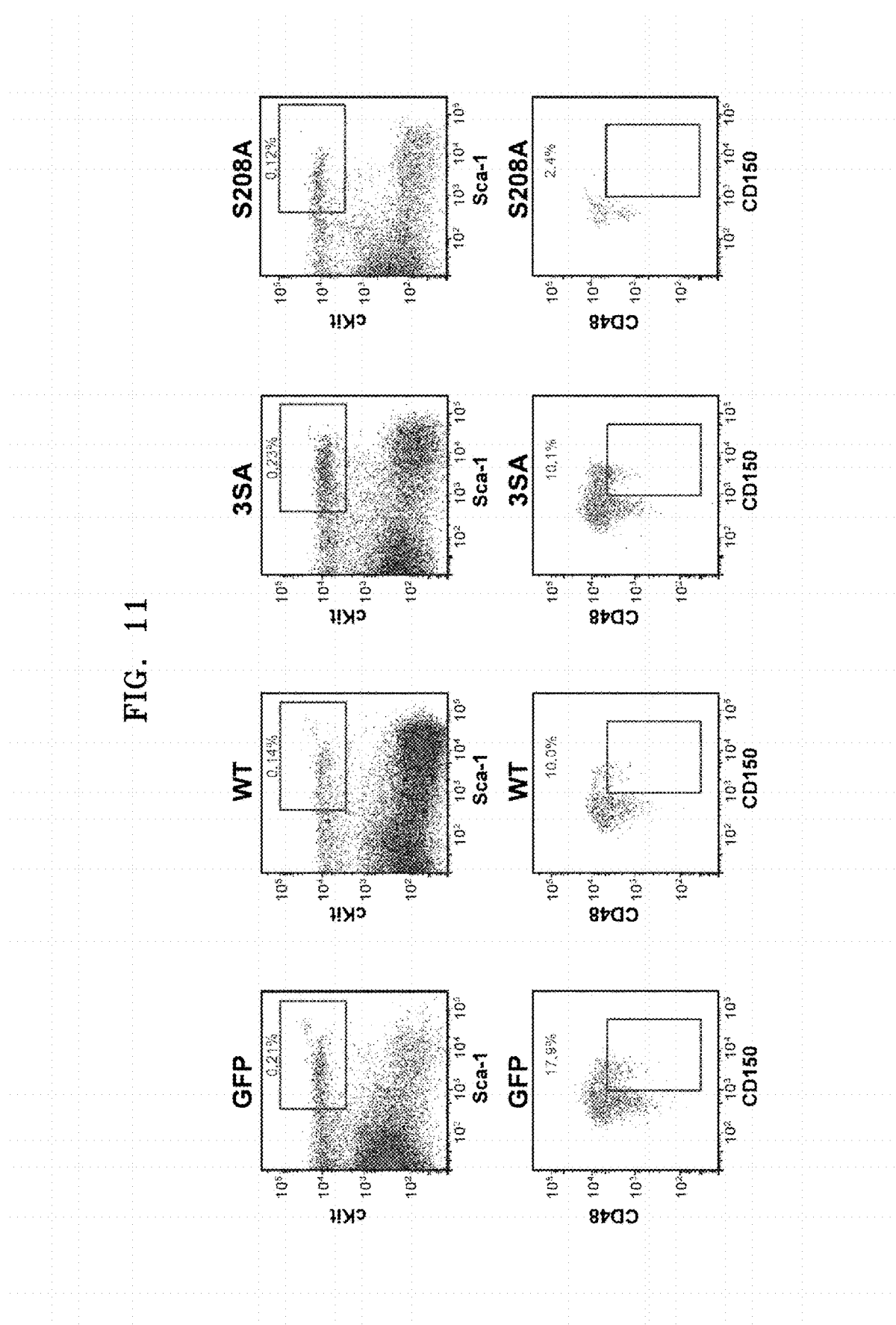
Figure 12:
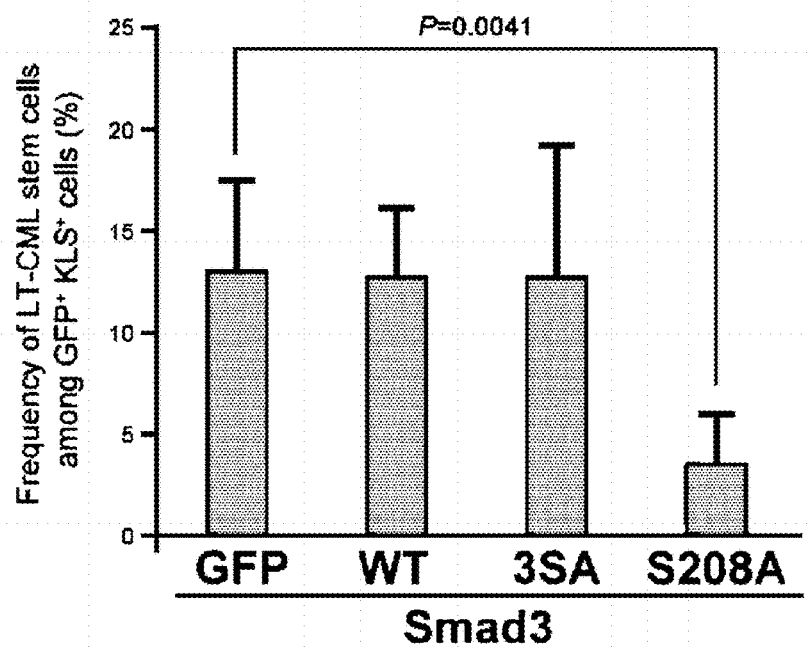
Figure 13A:
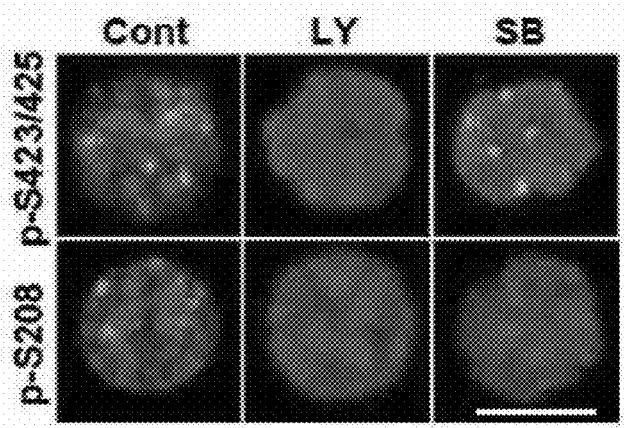
FIGS. 13 to 18 show that disruption of a nutrient supply essential for CML cancer stem cells may become a novel therapeutic approach.
Figure 13B:
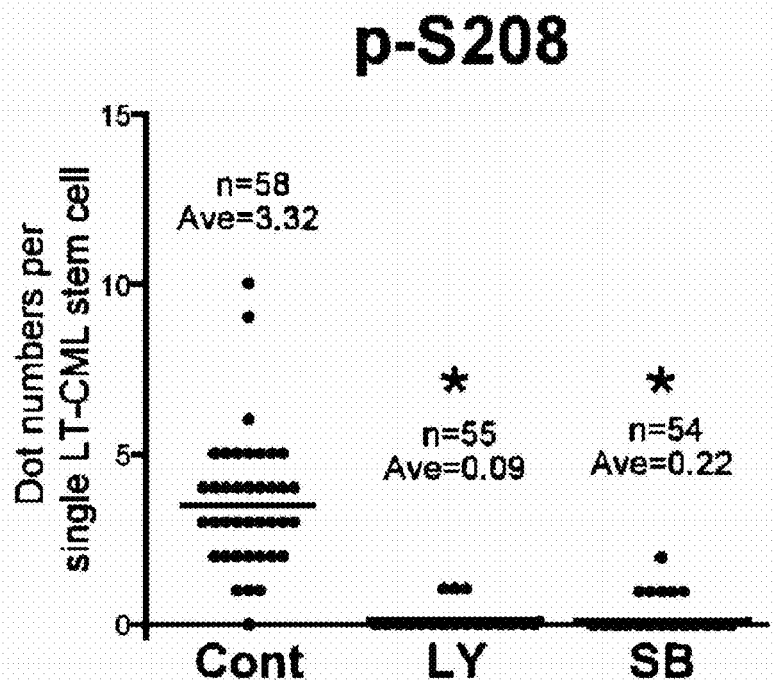

To investigate the relevance of Smad3 phosphorylation at Ser423/425 and Ser208, two mutant forms of human Smad3 that cannot be phosphorylated were used: Smad3 3SA, in which Ser422/423/425 are all converted to Ala; and Smad3 S208A, in which Ser208 is converted to Ala. $CML\text{-}KLS^+$ cells were infected with retroviral vectors expressing either control GFP, Smad3-wild type (WT), Smad3-3SA, or Smad3-S208A, and transplanted these cells into congenic recipient mice. CML cancer stem cell maintenance in vivo was then evaluated by flow cytometry. 30 days post transplantation, the Smad3 mutations had not affected the size of $GFP^+$(Smad3+) $CML\text{-}KLS^+$ cell population (top of FIG. 11). However, it was found that the frequency of the most primitive LT-CML cancer stem cells was markedly decreased in mice transplanted with $CML\text{-}KLS^+$ cells expressing Smad3-S208A (bottom of FIG. 11 and FIG. 12). Thus, inhibition of non-canonical Smad3-Ser208 phosphorylation in LT-CML cancer stem cells impairs their maintenance of self-renewal capacity in vivo.

Because both Smad3-Ser208 phosphorylation and Smad3-Foxo3a interaction were detectable only in LT-CML cancer stem cells (FIG. 10), it was investigate whether the phosphorylation of Smad3-Ser208 might be involved in regulating Foxo3a's recently reported function in CML cancer stem cells. Thus, it was analyzed whether suppression of LT-CML cancer stem cell colony-forming capacity induced by cefadroxil was reduced in Foxo3a-disrupted LT-CML cancer stem cells.

Figure 23A:
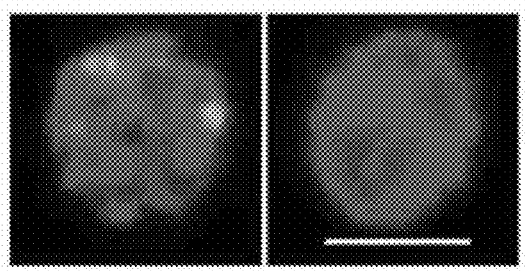
FIG. 23 shows D-PLA imaging and quantification result of interaction between phospho-Smad3-Ser208 and Foxo3a in Foxo3a$^{+/+}$ LT-CML stem cells. Foxo3a$^{-/-}$ LT-CML stem cells were used as a negative control.
Figure 23B:
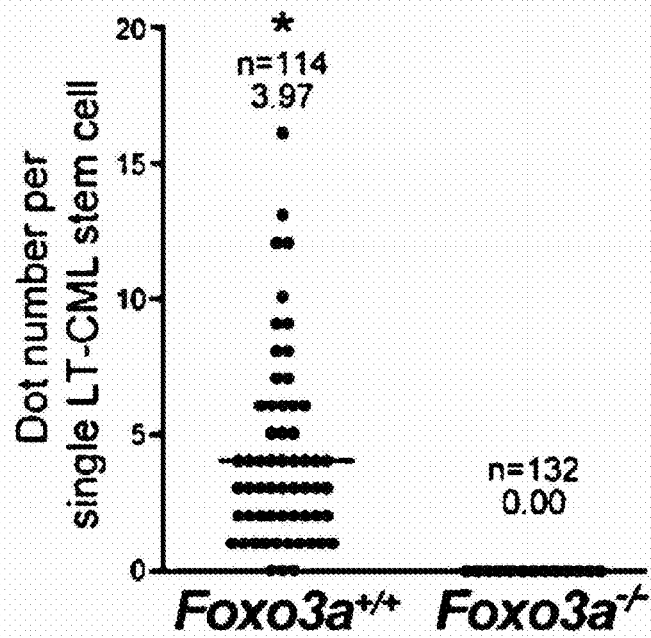

To establish a Foxo3a-deficient CML mouse model, Foxo3a−/−tet-inducible CML mice and Foxo3a+/+ littermate controls were generated. Then, LT-CML cancer stem cells were isolated from Foxo3a−/− and Foxo3a+/+ CML-affected littermates at 5 weeks post DOX withdrawal. Foxo3a−/−LT-CML stem cells exhibited a decrease in colony-forming capacity in vitro compared with Foxo3a+/+ LT-CML stem cells. However, the number of colonies formed by Foxo3a−/−LT-CML cancer stem cells was not altered by cefadroxil treatment. Furthermore, D-PLA revealed an interaction between phospho-Smad3-Ser208 and Foxo3a in Foxo3a+/+ LT-CML cancer stem cells, which did not occur in Foxo3a−/−LT-CML stem cells (FIG. 23). These results suggest that the Smad3-Ser208 phosphorylation by internalized dipeptides maintains CML cancer stem cells in a Foxo3a-dependent manner.

Figure 14A:
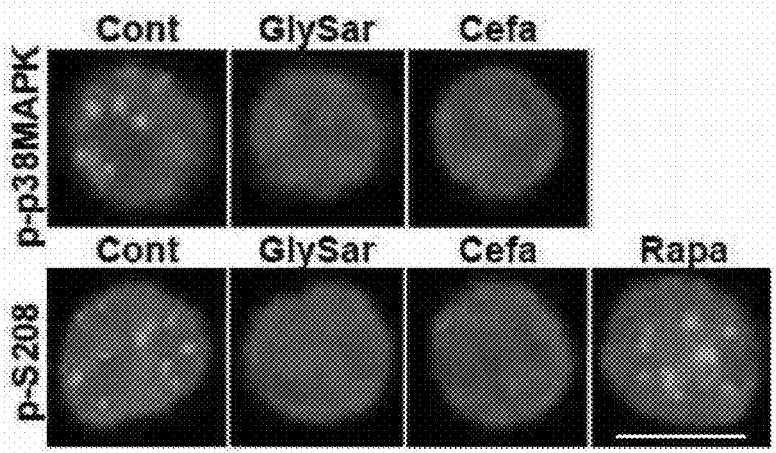
Figure 14B:
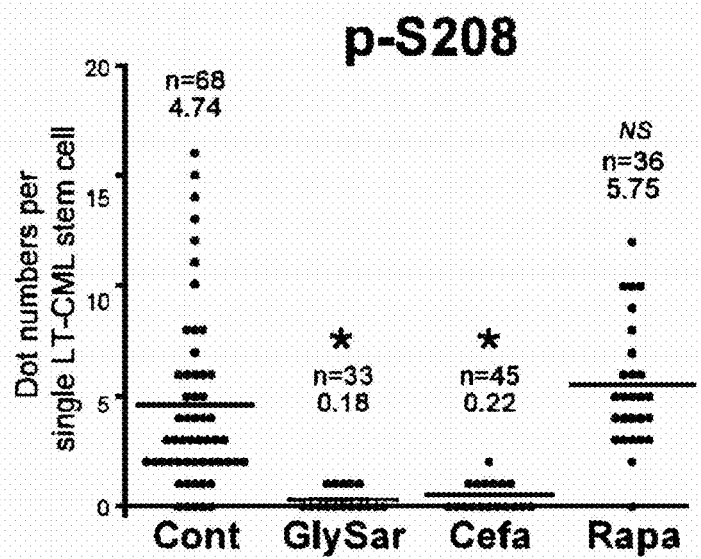
Figure 15A:
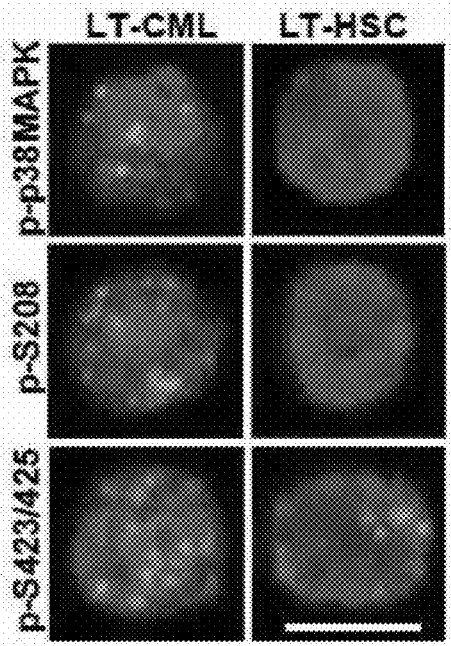
Figure 15B:
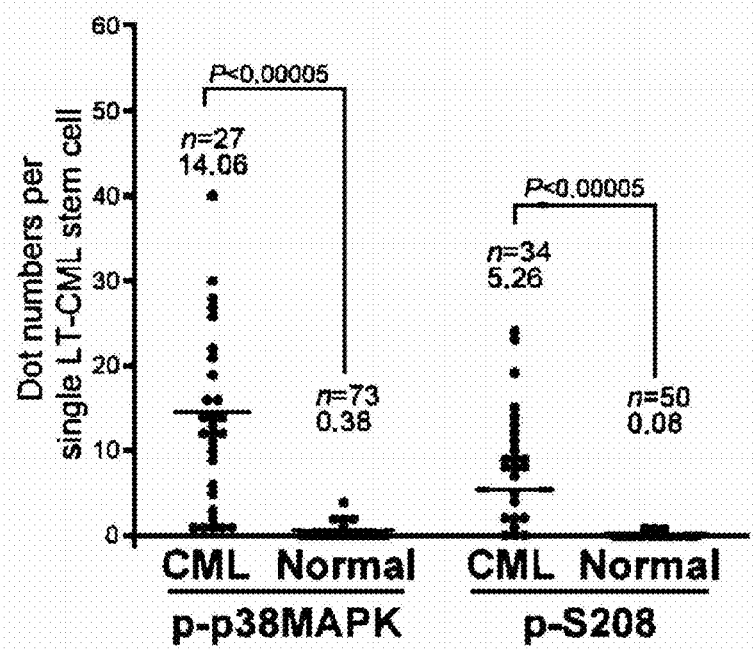

Because the Smad3 Ser208 phosphorylation is critical for LT-CML cancer stem cell maintenance, it was examined whether increased dipeptide uptake in cancer stem cells is associated with Smad3 Ser208 activation. Therefore, LT-CML cancer stem cells treated with either GlySar or cefadroxil were applied to D-PLA analysis. Interestingly, treatment of GlySar or cefadroxil blocked Smad3 Ser208 phosphorylation (FIG. 14). In contrast, treatment with rapamycin did not suppress Smad3 Ser208 phosphorylation, indicating that internalized dipeptides stimulate both mTORC1- and Smad3 Ser208-mediated nutrient signaling pathways in parallel. These results suggest that at least in LT-CML cancer stem cells, dipeptide species can induce activation of nutrient signaling through p38MAPK and drive its downstream phosphorylation of Smad3 Ser208.

To confirm that cefadroxil administration in vivo does not alter the function of normal HSCs, a well-established competitive reconstitution assay was employed. Irradiated CD45.2 recipient mice were co-transplanted with $1\times10^4$ purified normal $KLS^+$ cells derived from congenic CD45.1 mice+$5\times10^5$ unfractionated BM mononuclear cells (MNCs) derived from healthy CD45.2 mice. These animals then received daily administration of cefadroxil or vehicle for 8 weeks post transplantation. Importantly, there was no increase in the frequency of donor-derived CD45.1 MNCs in peripheral blood of recipients after 4 or 8 weeks of cefadroxil administration. Concomitantly, there was a comparable increase in the degree of chimerism originating from donor-derived normal $KLS^+$ cells, whether or not cefadroxil was present. Consequently, in vivo administration of cefadroxil has no detectable effect on the reconstitutive powers of normal HSCs.

Example 4

Dipeptide Nutrient Signaling Eradicates CML Stem Cells

Figure 24:
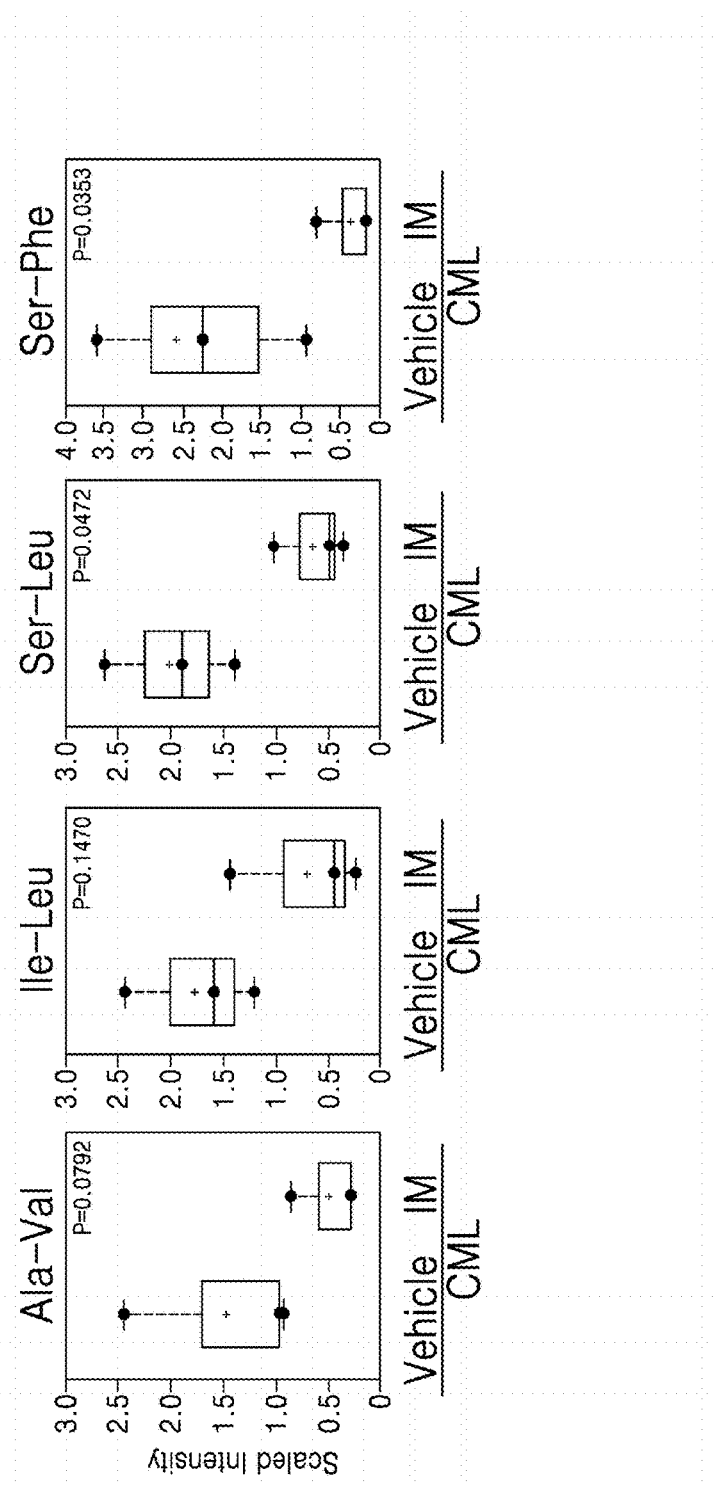
FIG. 24 shows metabolomic analyses of dipeptides in CML-KLS$^+$ cells derived from CML-affected mice (n=4 in each of three independent experiments) that received either vehicle or IM (100 mgKg$^{-1}$day$^{-1}$) for 30 days.

Specificity of dipeptide-induced nutrient signaling to LT-CML cancer stem cells prompted to investigate whether this pathway might be a possible therapeutic target, that is, whether disruption of dipeptide internalization might lead to the eradication of CML cancer stem cells and a reduction in disease relapse. First, to determine whether the SLC15A2 gene is upregulated in human CML patients as it is in CML-affected mice, data on levels of SLC15A2 were retrieved in cells of CML patients listed in a public database gene expression omnibus (GEO: GSE33075). Intriguingly, prior to IM therapy, SLC15A2 mRNA levels were higher in BM leukaemia cells of nine CML patients than in the BM haematopoietic cells of nine healthy individuals. However, after IM therapy, SLC15A2 mRNA levels in the same nine CML patients had decreased to a level comparable to that in healthy individuals. To further explore this finding, dipeptide levels were compared in $CML\text{-}KLS^+$ cells isolated from CML-affected mice that had received vehicle or IM therapy for 1 month. Consistent with the observations in human CML patients, metabolomic analysis of these mice indicated that IM treatment tended to decrease dipeptide levels in $CML\text{-}KLS^+$ cells (FIG. 24). In addition, IM treatment of murine LT-CML stem cells in vitro reduced levels of phospho-Smad3-Ser208. These results suggest that accumulation of dipeptide species may not be the direct cause of TKI-resistance in the CML cancer stem cell population responsible for disease recurrence. However, the findings also suggest that the SLC15A2-mediated nutrient supply identified herein plays a critical role in human CML leukaemogenesis.

Figure 16:
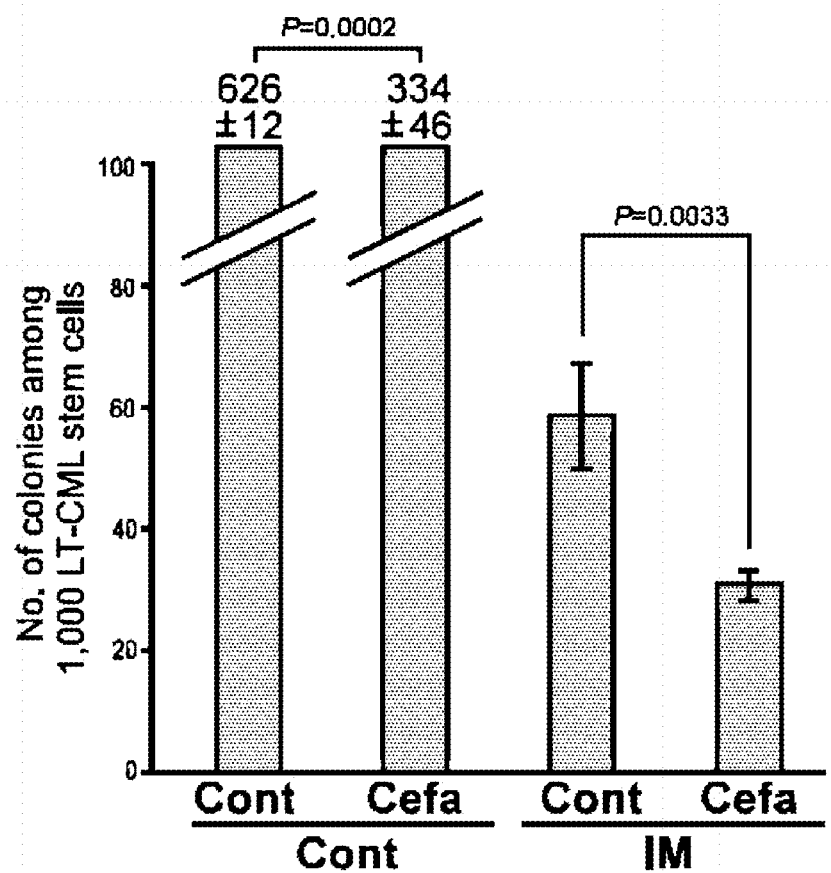
Figure 17:
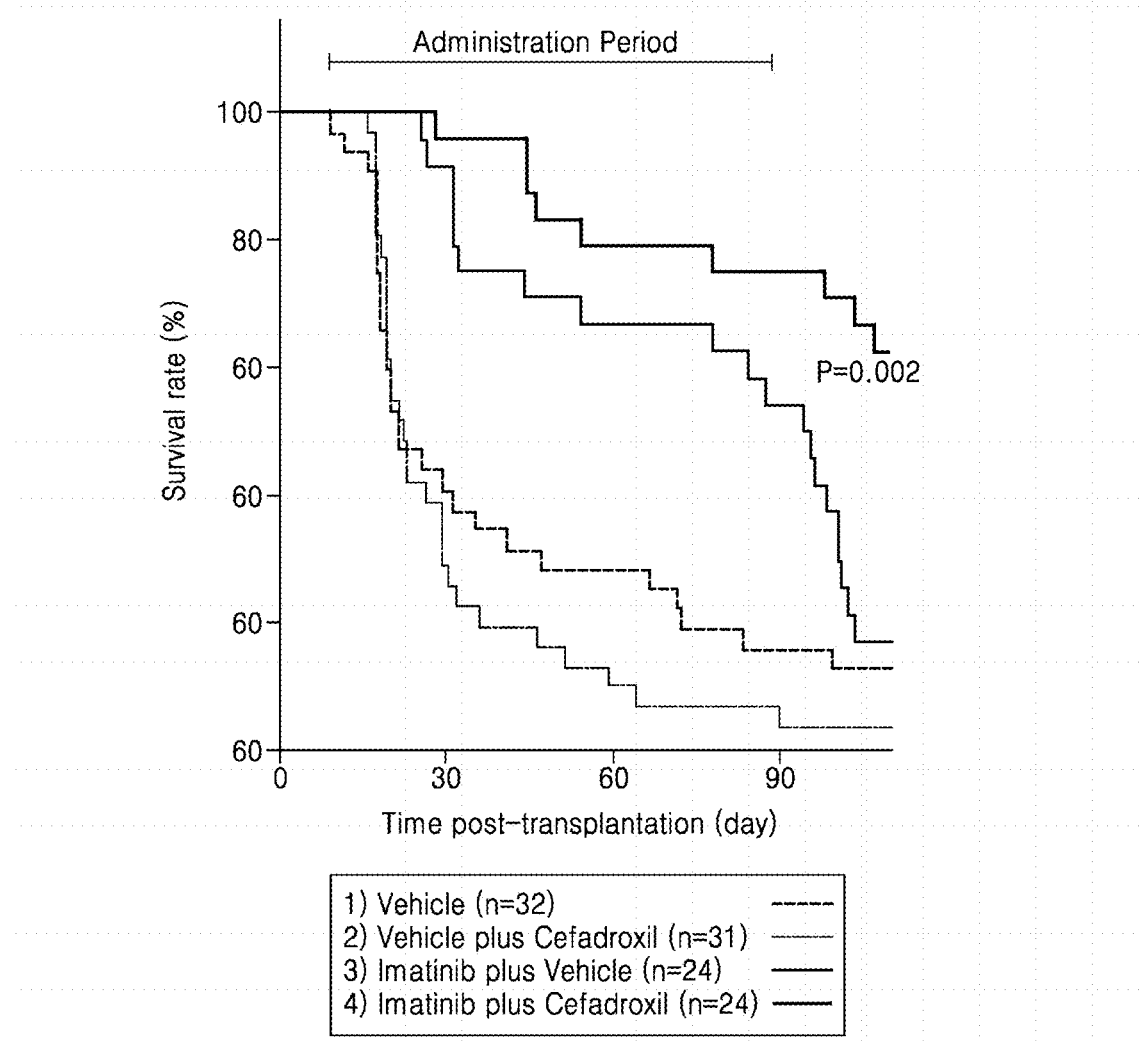
Figure 18:
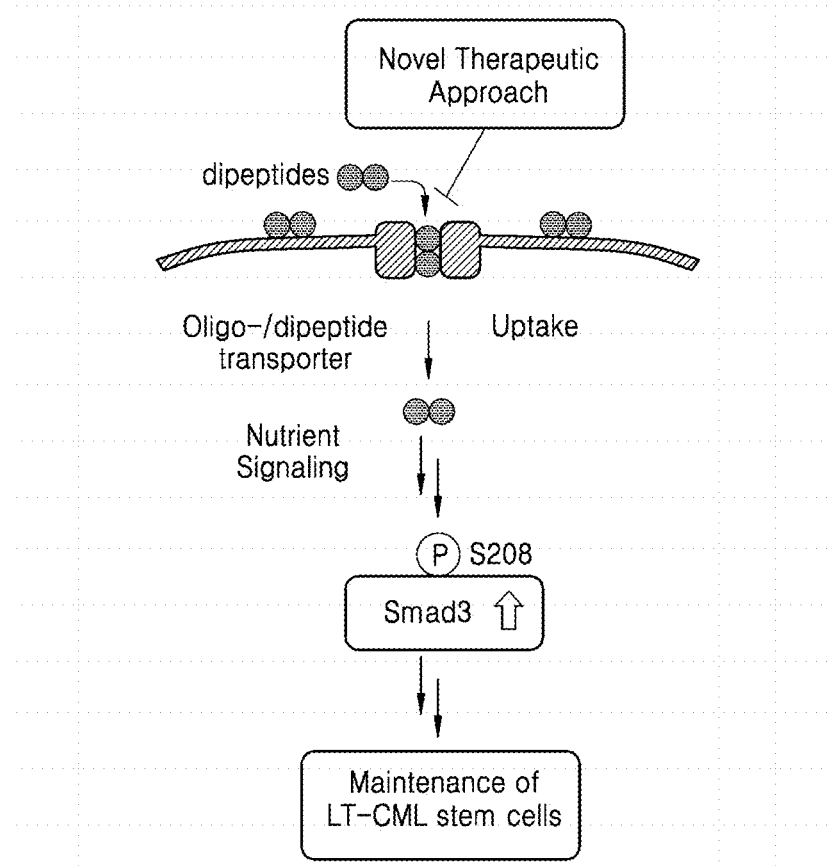

Next, it was evaluated the potential therapeutic benefit of combined administration of TKI, which blocks the activity of BCR-ABL1 kinase, together with cefadroxil, which inhibits Slc15A2-mediated nutrient signaling. When murine LT-CML cancer stem cells were cultured in vitro with cefadroxil+IM, colony formation was reduced compared with treatment with IM alone (FIG. 16). Treatment of CML-affected mice with IM alone in vivo delayed disease onset compared with the vehicle-treated group, but, as expected, these animals eventually experienced recurrence of BCR-ABL1+ disease after discontinuation of the therapy (FIG. 17). Curiously, administration of cefadroxil alone appeared to promote disease development. However, the combined administration of IM+cefadroxil significantly reduced the recurrence rate of BCR-ABL1+ disease, as compared with the group treated with IM alone (FIG. 17).

Figure 25:
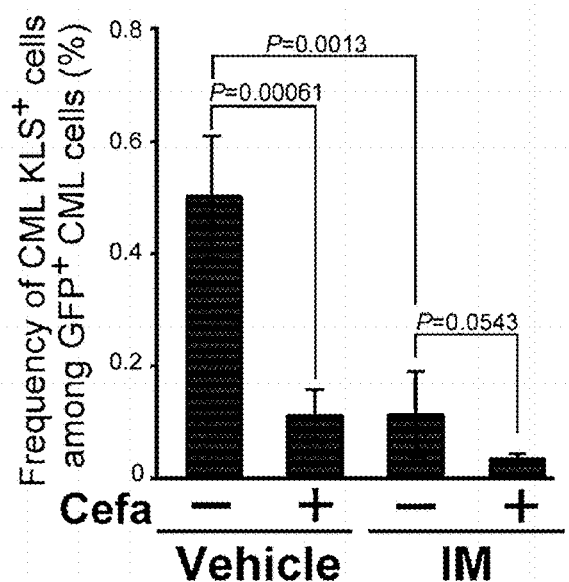
FIGS. 25 and 26 show that inhibition of dipeptide uptake reduces CML cancer stem cells in CML-affected mice received vehicle (−), vehicle+IM, vehicle+Cefa (+), or IM+Cefa daily for 30 days post transplantation.
Figure 26:
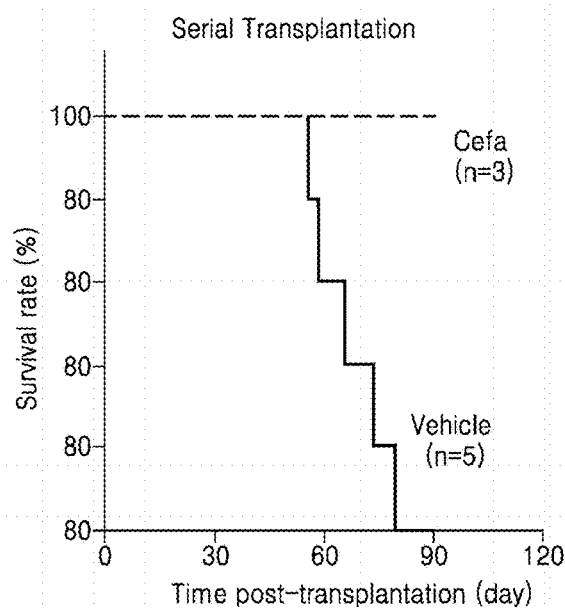

It was determined whether cefadroxil administration could in fact eradicate the most primitive CML cancer stem cells in CML-affected mice in vivo. Indeed, the number of CML-KLS$^+$ cells among GFP/BCR-ABL1+CML cells isolated from BM of CML-affected mice was significantly decreased by cefadroxil exposure in vivo (FIGS. 25-26). Although IM alone also reduced the number of CML-KLS$^+$ cells, the combined administration of IM+cefadroxil had a much greater repressive effect on this population (FIG. 25).

Notably, in serial transplantation experiments, CML-KLS$^+$ cells isolated from cefadroxil-treated CML-affected mice completely lost their ability to drive BCR-ABL1+ disease in new recipients, allowing the animals to survive for over 90 days (FIG. 26). In contrast, all mice that received CML-KLS$^+$ cells from vehicle-treated CML-affected animals developed BCR-ABL1+ disease and died before 80 days, demonstrating that the untreated CML-KLS$^+$ cells had retained their CML-initiating ability. These results indicate that oral administration of cefadroxil to inhibit dipeptide uptake may block nutrient signaling important for the maintenance of CML cancer stem cells in vivo, and further suggest that cefadroxil used in combination with TKI can improve the survival of CML-affected mice by eradicating CML cancer stem cells.

Figure 27:
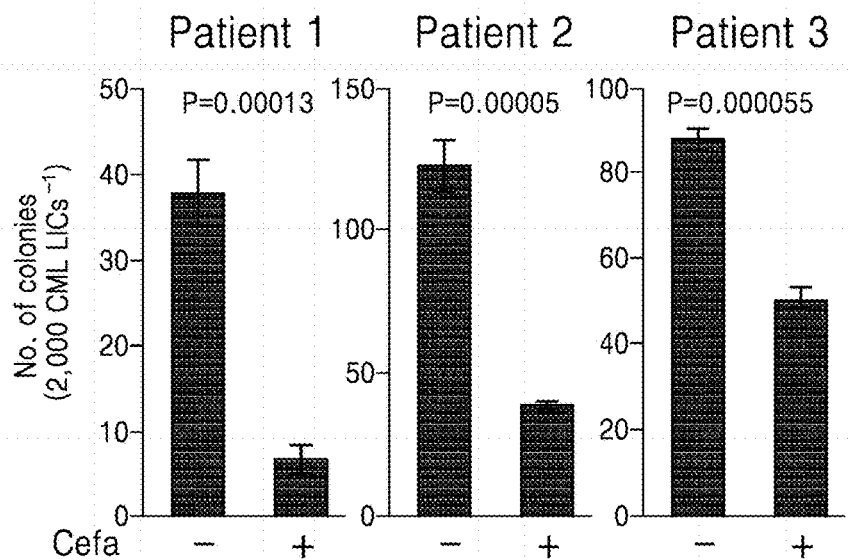
FIGS. 27 and 28 show quantification result of colony-forming capacity of human CD34$^+$CD38$^-$Lin$^-$CML-LICs.
Figure 28:
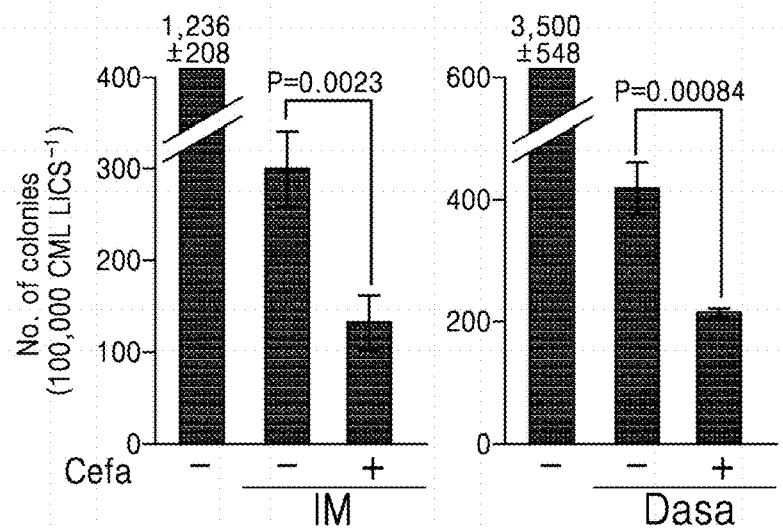

Lastly, to investigate the relevance of our findings to human CML therapy, the effects of cefadroxil treatment in vitro on CML-LICs obtained from human chronic phase CML patients were evaluated. CD34$^+$CD38$^-$Lin$^-$CML-LICs were isolated from BM MNCs of three CML patients, and these cells were treated in vitro with cefadroxil. As expected, cefadroxil suppressed the colony-forming capacity of all three human CML-LIC samples in vitro (FIG. 27). Importantly, co-treatment of human CML-LICs with a combination of TKI (IM or dasatinib)+cefadroxil significantly reduced colony formation over the suppressive effect of the TKI alone (FIG. 28). Collectively, these results indicate that nutrient signaling through Smad3 activated by internalized dipeptide species is essential for CML cancer stem cell activity. Thus, this nutrient supply and its downstream signaling pathway may offer novel candidate therapeutic targets for eradicating CML cancer stem cells. These data suggest that inhibitors of this pathway used in combination with TKI therapy may provide concrete clinical benefits for human CML patients.

The invention claimed is:

1. A method of treating chronic myelogenous leukemia (CML) in a subject, comprising administering to the subject a pharmaceutical composition for treating CML, the pharmaceutical composition comprising a substance blocking nutrient signaling of CML cancer stem cells as an active ingredient and a pharmaceutically acceptable carrier, wherein the substance blocking nutrient signaling of CML cancer stem cells is a dipeptide transporter inhibitor, wherein the dipeptide transporter inhibitor is one or more selected from the group consisting of cefadroxil and GlySar in combination with a tyrosine kinase inhibitor as an active ingredient, wherein the tyrosine kinase inhibitor is one or more selected from the group consisting of imatinib, nilotinib, dasatinib, bosutinib, and pharmaceutically acceptable salts thereof.

2. The method of claim 1, wherein the dipeptide transporter is encoded by Slc15a2 gene.

3. The method of claim 1, wherein the substance blocking nutrient signaling of CML cancer stem cells inhibits phosphorylation of Ser208 of Smad3.

4. The method of claim 1, wherein the substance blocking nutrient signaling of CML cancer stem cells is a substrate specific to Slc15a2 protein, and inhibit dipeptide transport function of Slc15a2.

5. The method of claim 1, wherein the chronic myelogenous leukemia is caused by CML cancer stem cells.

6. The method of claim 1, wherein the chronic myelogenous leukemia is recurred by Bcr-Abl tyrosine kinase resistance.

* * * * *